(12) United States Patent
Polster et al.

(10) Patent No.: US 9,622,727 B2
(45) Date of Patent: Apr. 18, 2017

(54) TISSUE SAMPLING DEVICE

(71) Applicant: THE CLEVELAND CLINIC FOUNDATION, Cleveland, OH (US)

(72) Inventors: Joshua M. Polster, Shaker Hts., OH (US); Grant Hoffman, Akron, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 321 days.

(21) Appl. No.: 14/205,830

(22) Filed: Mar. 12, 2014

(65) Prior Publication Data
US 2014/0276202 A1    Sep. 18, 2014

Related U.S. Application Data

(60) Provisional application No. 61/783,101, filed on Mar. 14, 2013.

(51) Int. Cl.
*A61B 10/02*    (2006.01)

(52) U.S. Cl.
CPC .............................. *A61B 10/0266* (2013.01)

(58) Field of Classification Search
CPC ..... A61B 10/02; A61B 10/0266; A61B 17/32; A61B 2017/320028
See application file for complete search history.

(56) References Cited

U.S. PATENT DOCUMENTS

| 2,816,552 A | 12/1957 | Hoffman | |
| 3,705,577 A | 12/1972 | Sierra | |
| 5,271,414 A * | 12/1993 | Partika | A61B 10/0266 600/567 |
| 5,449,001 A * | 9/1995 | Terwilliger | A61B 10/0275 600/567 |
| 5,709,697 A | 1/1998 | Ratcliff et al. | |
| 5,833,628 A | 11/1998 | Yuan et al. | |
| 7,914,463 B2 * | 3/2011 | Tarter | A61B 10/0275 600/567 |
| D657,461 S * | 4/2012 | Schembre | A61B 10/0275 D24/130 |

(Continued)

FOREIGN PATENT DOCUMENTS

WO    2010123823 A1    10/2010

*Primary Examiner* — Adam J Eiseman
*Assistant Examiner* — Yasmeen S Warsi
(74) *Attorney, Agent, or Firm* — Tarolli, Sundheim, Covell & Tummino LLP

(57) ABSTRACT

A tissue sampling device includes for removing tissue from a target area in the body comprises a shaft having an outer surface. Two first portions and two second portions of the outer surface extend lengthwise of the shaft. Each first portion of the outer surface is associated with a different second portion and is spaced apart from its associated second portion. Each first portion of the outer surface at least partially defines a cutting edge extending in a straight line lengthwise of the shaft. Each first portion of the outer surface and its associated second portion are associated with a tissue-receiving surface extending lengthwise of the shaft. Each tissue-receiving surface defines a depression for receiving a tissue sample removed from the target area by the cutting edge of the associated first portion of the outer surface when the shaft is rotated about its longitudinal axis in the target area.

19 Claims, 16 Drawing Sheets

(56) References Cited

U.S. PATENT DOCUMENTS

| | | | |
|---|---|---|---|
| 8,882,681 B2* | 11/2014 | Neoh | A61B 10/0275 |
| | | | 600/566 |
| 8,936,557 B2* | 1/2015 | Al-Mohizea | A61B 10/0233 |
| | | | 600/567 |
| 9,226,734 B2* | 1/2016 | Eells | A61B 10/0275 |
| 2007/0016101 A1* | 1/2007 | Feldman | A61B 10/0275 |
| | | | 600/567 |
| 2007/0208273 A1 | 9/2007 | Vetter et al. | |
| 2008/0114265 A1* | 5/2008 | Tarter | A61B 10/0275 |
| | | | 600/567 |
| 2009/0018467 A1* | 1/2009 | Chiu | A61B 10/0266 |
| | | | 600/562 |
| 2010/0280407 A1* | 11/2010 | Polster | A61B 10/0266 |
| | | | 600/566 |
| 2012/0245487 A1* | 9/2012 | Eells | A61B 10/0275 |
| | | | 600/567 |

* cited by examiner

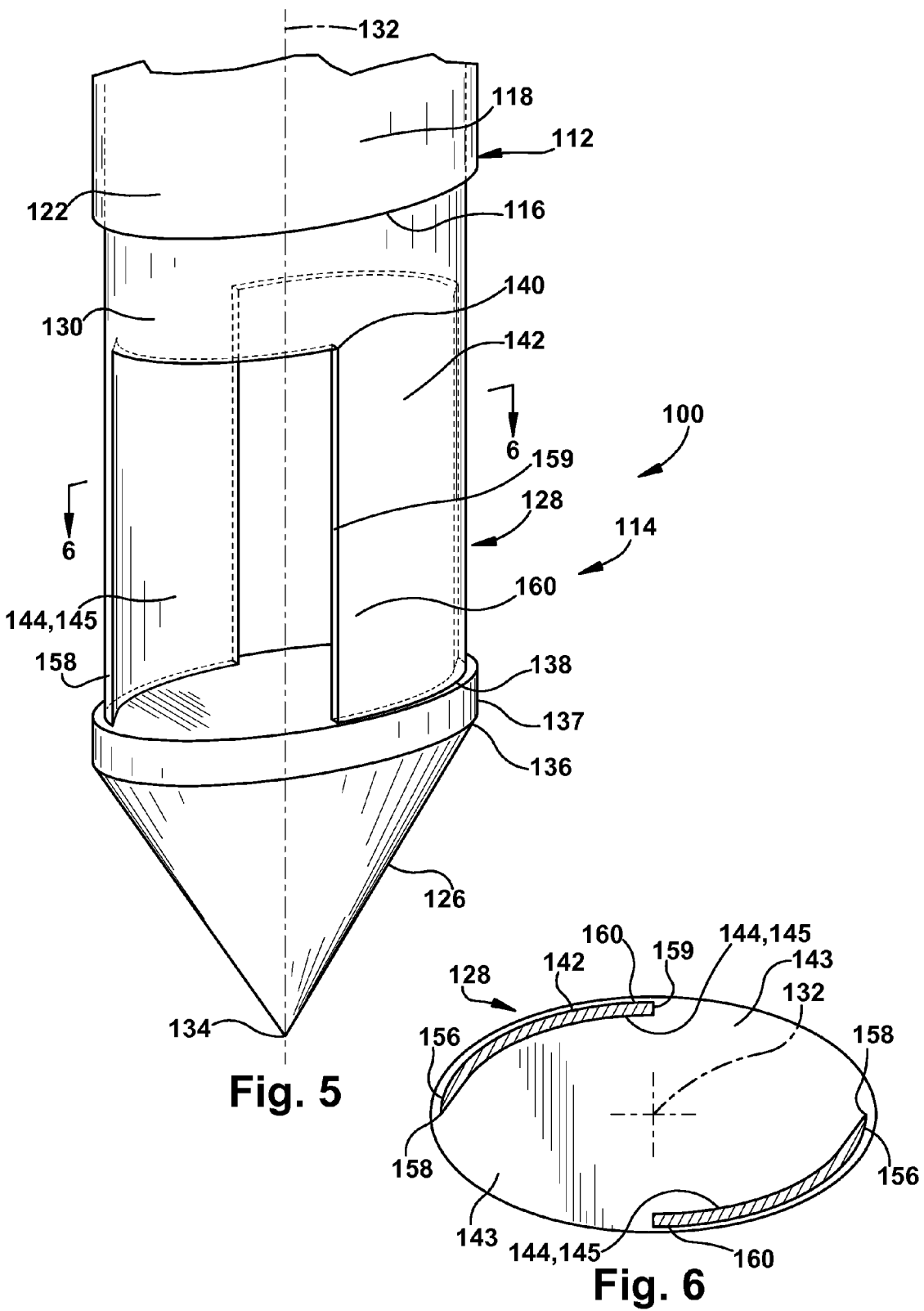

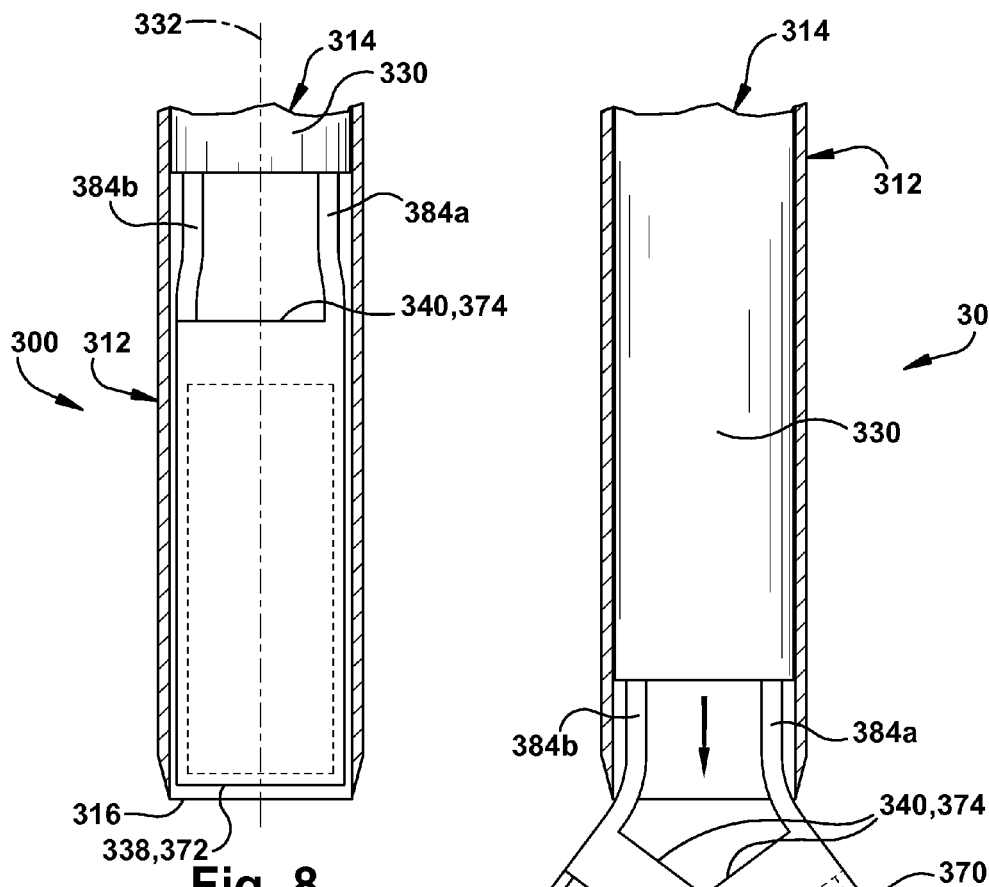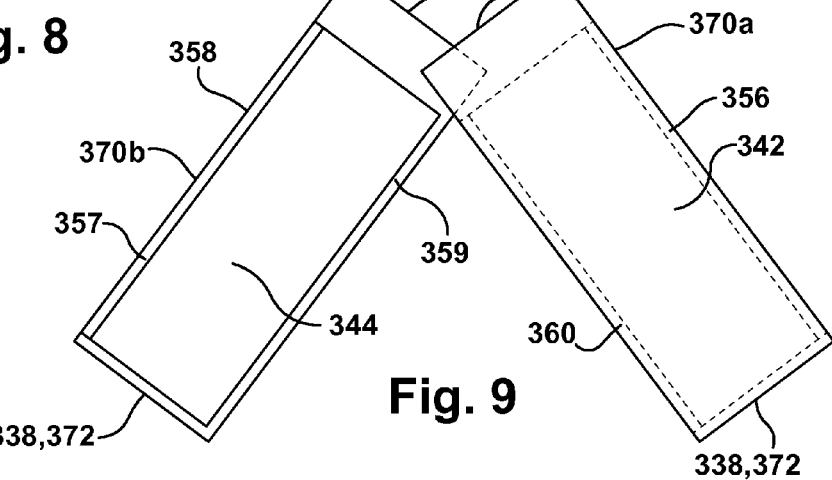

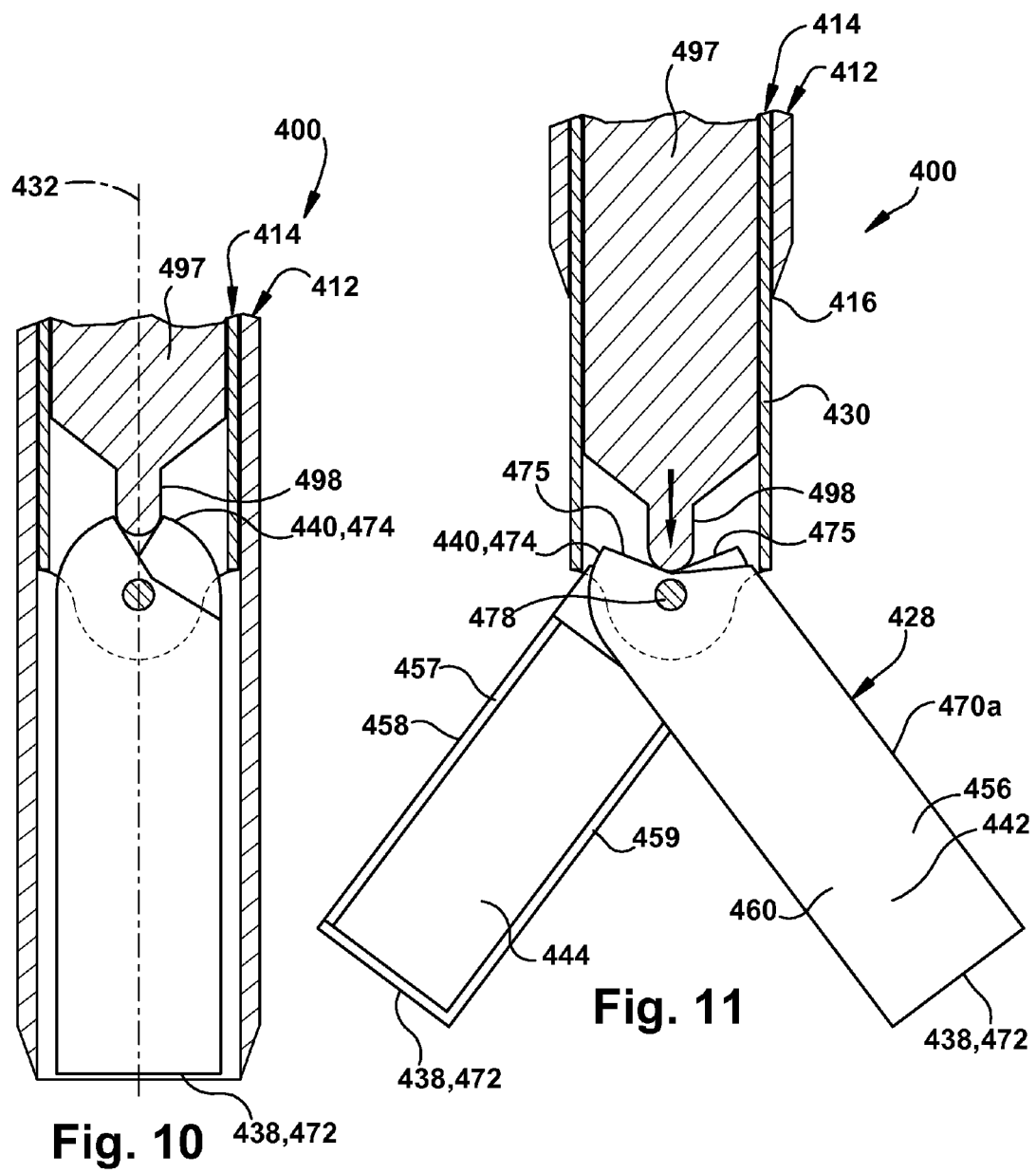

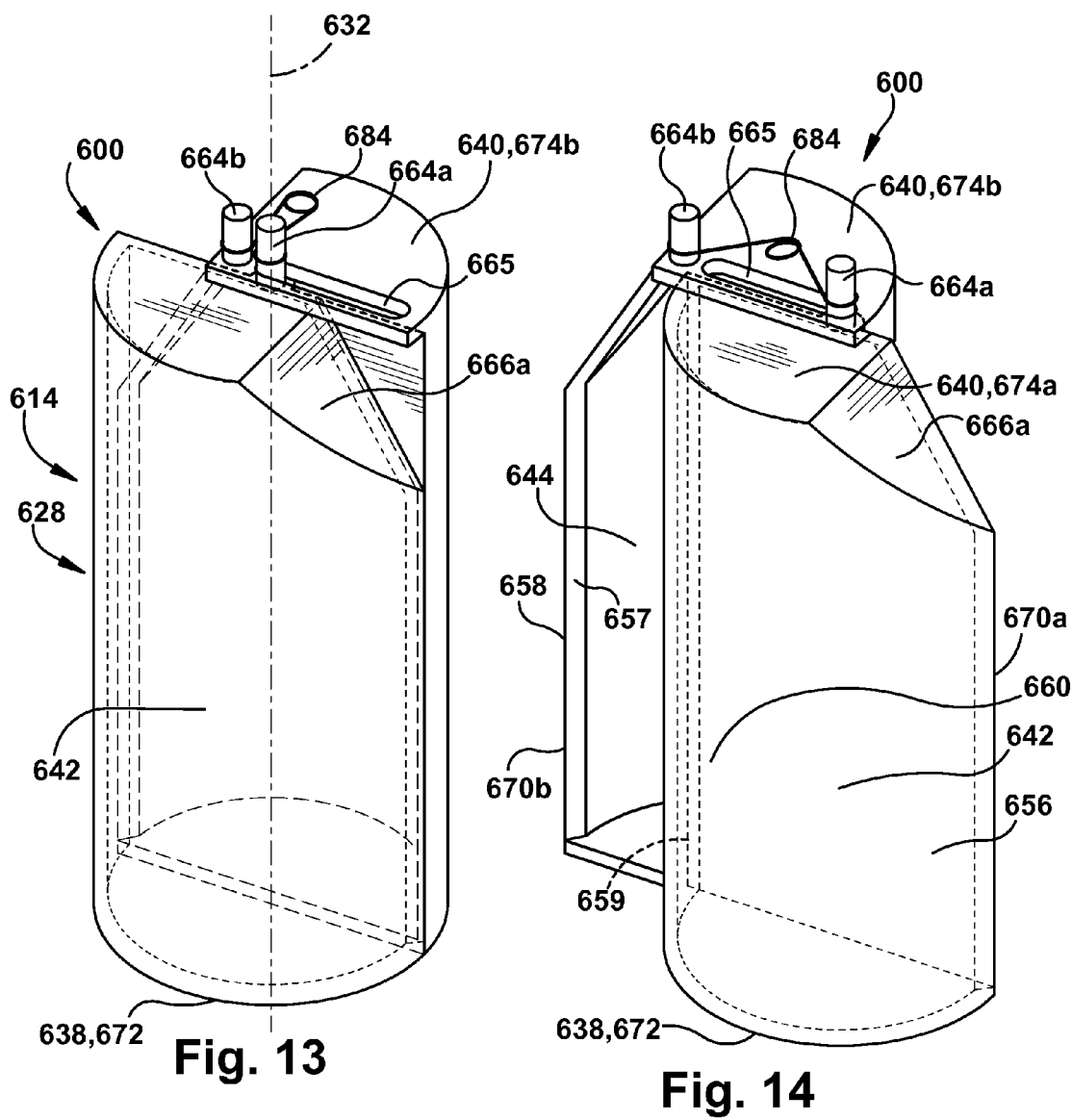

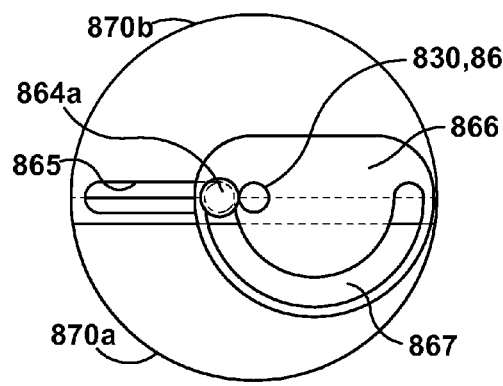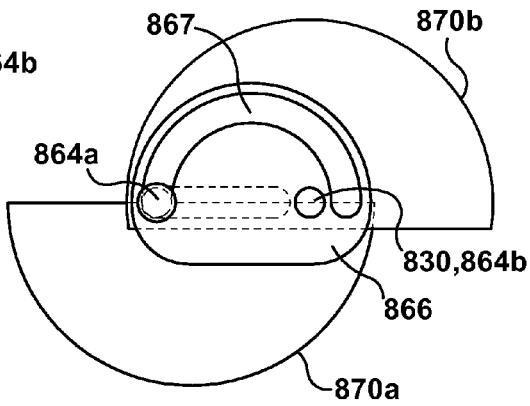
Fig. 17　　　　Fig. 18
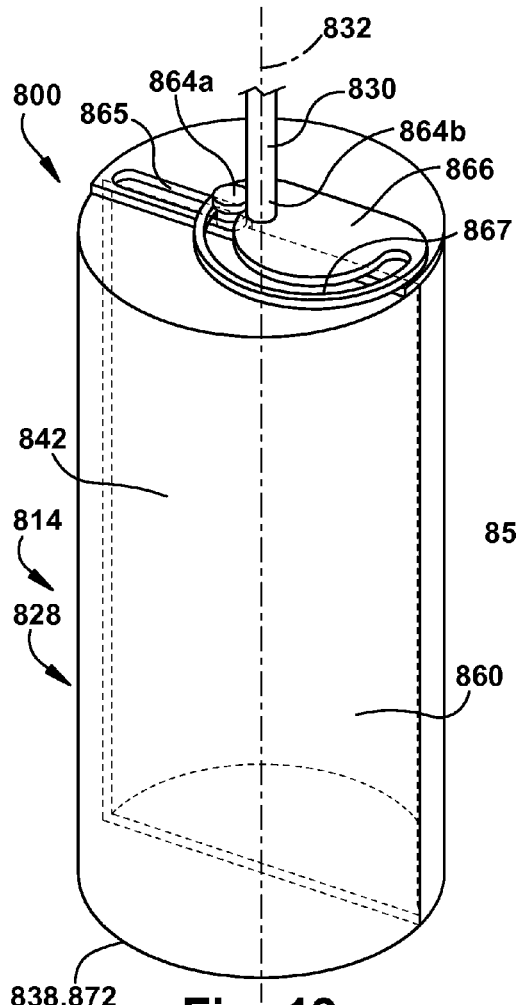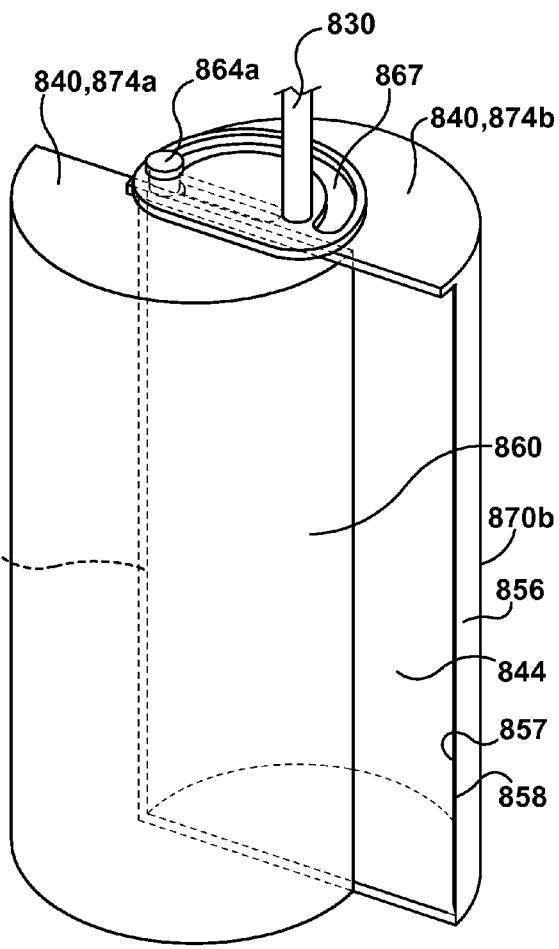
Fig. 19　　　　Fig. 20

TISSUE SAMPLING DEVICE

CROSS-REFERENCE TO RELATED APPLICATION

The present application claims priority to U.S. Provisional Application No. 61/783,101, filed on Mar. 14, 2013, which is incorporated by reference herein.

FIELD OF THE INVENTION

The present invention relates to a tissue sampling device and, more particularly, to a biopsy device with an elliptical outer shape.

BACKGROUND OF THE INVENTION

Testing suspicious or otherwise targeted tissue for cancerous growths and/or other indicia is commonly done by taking a sample or specimen of the tissue in a procedure called a biopsy. The tissue sample is removed from a patient's body and diagnostic tests are performed on the tissue sample in order to determine, for example, whether malignant cell growth is present. A biopsy is commonly performed by inserting a needle into the targeted area. The needle cuts the tissue sample and simultaneously collects it so that the sample can be removed from the body. It is desirable to collect as large a volume of tissue as possible from the targeted area, while minimizing the time consumed by the procedure and the discomfort to the patient.

SUMMARY OF THE INVENTION

The present invention is directed to a tissue sampling device and, more particularly, to a biopsy device with an elliptical outer shape.

In accordance with an embodiment of the present invention, a tissue sampling device includes for removing tissue from a target area in the a body comprises a shaft having a proximal end, a distal end, and a central longitudinal axis extending from the proximal end to the distal end. The shaft also has a length extending in a direction along the longitudinal axis. An outer surface of the shaft extends lengthwise of the shaft. The outer surface includes two first portions extending lengthwise of the shaft and two second portions extending lengthwise of the shaft. Each first portion of the outer surface is associated with a different second portion and is spaced apart from its associated second portion by a predetermined distance. Each first portion of the outer surface at least partially defines a cutting edge extending in a straight line lengthwise of the shaft. The shaft further includes two tissue-receiving surfaces extending lengthwise of the shaft. Each first portion of the outer surface and its associated second portion are associated with a different tissue-receiving surface. Each tissue-receiving surface defines a depression for receiving a sample of tissue removed from the target area by the cutting edge defined by its associated first portion of the outer surface when the shaft is rotated about its longitudinal axis in the target area. Each tissue-receiving surface extends from adjacent its associated first portion of the outer surface toward its associated second portion of the outer surface for a majority of the predetermined distance between its associated first portion and its associated second portion and provides a continuous surface free of any opening.

In accordance with another embodiment of the present invention, a tissue sampling device includes for removing tissue from a target area in a body comprises a shaft having a proximal end, a distal end, and a central longitudinal axis extending from the proximal end to the distal end. The shaft also has a length extending in a direction along the longitudinal axis. An outer surface of the shaft extends lengthwise of the shaft. The outer surface includes two first portions extending lengthwise of the shaft and two second portions extending lengthwise of the shaft. Each first portion of the outer surface is associated with a different second portion and is spaced apart from its associated second portion by a predetermined distance. Each first portion of the outer surface at least partially defines a cutting edge extending lengthwise of the shaft. The shaft further includes two tissue-receiving surfaces extending lengthwise of the shaft. Each first portion of the outer surface and its associated second portion are associated with a different tissue-receiving surface. Each tissue-receiving surface defines a depression for receiving a sample of tissue removed from the target area by the cutting edge defined by its associated first portion of the outer surface when the shaft is rotated about its longitudinal axis in the target area. Each tissue-receiving surface extends from adjacent its associated first portion of the outer surface toward its associated second portion of the outer surface for a majority of the predetermined distance between its associated first portion and its associated second portion and provides a continuous surface free of any opening. The outer surface of the shaft has a generally elliptical shape when viewed in cross section taken perpendicular to the longitudinal axis. The elliptical shape has a major axis and a minor axis. Each cutting edge is located at the outer surface adjacent the major axis of the elliptical shape.

In accordance with a further embodiment of the present invention, a tissue sampling device for removing tissue from a target area in a body comprises a shaft having a proximal end, a distal end, and a central longitudinal axis extending from the proximal end to the distal end. The shaft also has a length extending in a direction along the longitudinal axis. The outer surface includes two first portions extending lengthwise of the shaft and two second portions extending lengthwise of the shaft. Each first portion of the outer surface is associated with a different second portion and is spaced apart from its associated second portion by a predetermined distance. Each first portion of the outer surface at least partially defines a cutting edge extending in a straight line lengthwise of the shaft. The shaft further includes two tissue-receiving surfaces extending lengthwise of the shaft. Each first portion of the outer surface and its associated second portion are associated with a different tissue-receiving surface. Each tissue-receiving surface defines a depression for receiving a sample of tissue removed from the target area by the cutting edge defined by its associated first portion of the outer surface when the shaft is rotated about its longitudinal axis in the target area. Each tissue-receiving surface extends from adjacent its associated first portion of the outer surface toward its associated second portion of the outer surface for a majority of the predetermined distance between its associated first portion and its associated second portion and provides a continuous surface free of any opening. Each tissue-receiving surface and each cutting edge is movable radially relative to a portion of the shaft adjacent the proximal end of the shaft while maintaining the cutting edge in a straight line.

BRIEF DESCRIPTION OF THE DRAWINGS

The foregoing and other features and advantages of the present invention will become apparent to those skilled in the art to which the present invention relates upon reading the following description with reference to the accompanying drawings, in which:

FIG. 5 is a perspective view of a tissue sampling device in accordance with a second embodiment of the present invention;

FIG. 6 is a top sectional view of the tissue sampling device of FIG. 5 taken along line 6-6 of FIG. 5;

FIG. 8 is a perspective view of a tissue sampling device in accordance with a fourth embodiment of the present invention in a first stage of deployment;

FIG. 9 is a perspective view of the tissue sampling device of FIG. 8 in a second stage of deployment;

FIG. 10 is a perspective view of a tissue sampling device in accordance with a fifth embodiment of the present invention in a first stage of deployment;

FIG. 11 is a perspective view of the tissue sampling device of FIG. 10 in a second stage of deployment;

FIG. 13 is a perspective view of a tissue sampling device in accordance with a seventh embodiment of the present invention in a first stage of deployment;

FIG. 14 is a perspective view of the tissue sampling device of FIG. 13 in a second stage of deployment;

FIG. 17 is a top view of a tissue sampling device in accordance with a tenth embodiment of the present invention in a first stage of deployment;

FIG. 18 is a top view of the tissue sampling device of FIG. 17 in a second stage of deployment;

FIG. 19 is a perspective view of the tissue sampling device of FIG. 17 in its first stage of deployment;

FIG. 20 is a perspective view of the tissue sampling device of FIG. 17 in its second stage of deployment;

DETAILED DESCRIPTION

Figure 1:
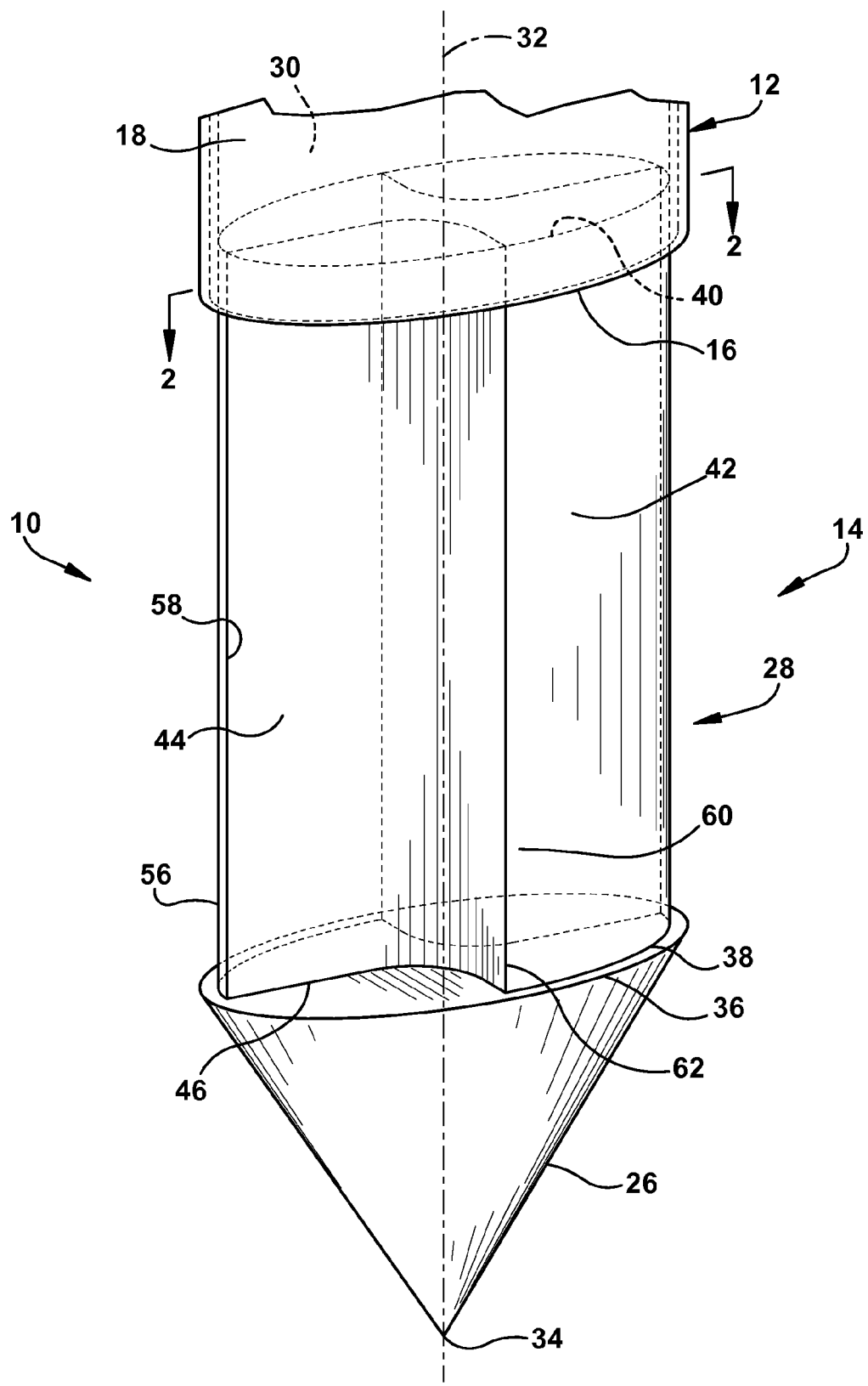
FIG. 1 is a perspective view of a tissue sampling device in accordance with a first embodiment of the present invention.
Figure 2:
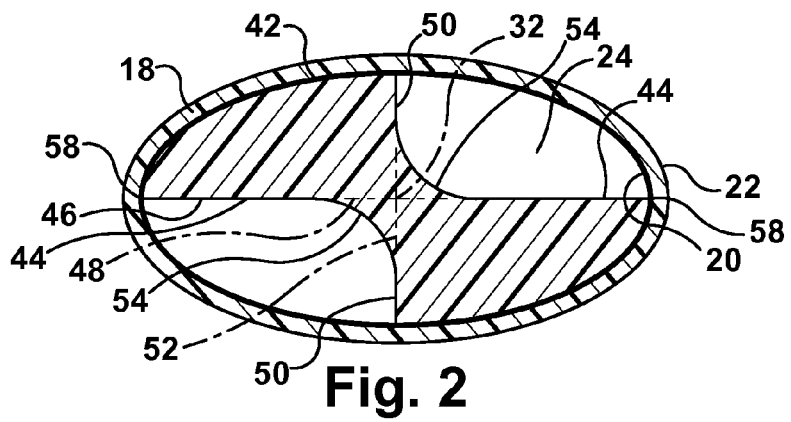
FIG. 2 is a top sectional view of the tissue sampling device of FIG. 1 taken along line 2-2 of FIG. 1.
Figure 3:
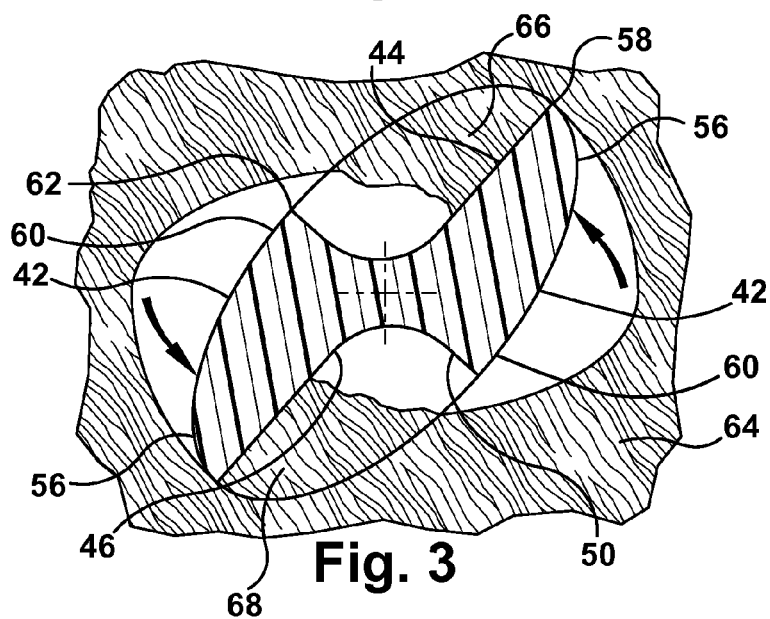
FIG. 3 is a view similar to FIG. 2 showing the tissue sampling device of FIG. 1 in a first step of collecting a tissue sample.

FIGS. 1 through 4 illustrate a tissue sampling device 10, in accordance with an example of the present invention. The tissue sampling device 10 includes a tubular cannula or outer sheath 12 and a coaxial inner shaft 14. The outer sheath 12 has a proximal end (not shown), a distal end 16, and a tubular body 18 extending between the proximal end and the distal end. The distal end 16 is sharpened to provide a cutting edge. As shown in FIG. 2, the body 18 of the outer sheath 12 has an inner surface 20 and a substantially concentric outer surface 22. Both the inner surface 20 and the outer surface 22 extend the length of the outer sheath 12 between the distal end 16 and the proximal end (not shown). The outer sheath 12, including the inner surface 20 and the outer surface 22 of the body 18 of the outer sheath, has an elliptical shape when viewed in a cross-section taken radially or perpendicular to the length of the outer sheath. The inner surface 20 defines a passage 24, which extends from the open distal end 16 of the outer sheath 12 to the proximal end (not shown). The outer sheath 12 may be fabricated from any suitable biocompatible material, such as titanium, stainless steel, plastic, ceramic or combinations of such materials.

The inner shaft 14 includes a pointed distal tip 26, a cutting head 28, and a proximal connecting portion 30. A central longitudinal axis 32 of the inner shaft 14 extends through the distal tip 26, the cutting head 28, and the proximal connecting portion 30. The inner shaft 14 is a solid member throughout its length, which extends in a direction along the central longitudinal axis 32. The inner shaft 14 may be fabricated from any suitable biocompatible material, such as titanium, stainless steel, plastic, ceramic or combinations of such materials, so long as the cutting head can be formed with sharpened edges, as explained below, for cutting tissue samples. The proximal connecting portion 30, at least, of the inner shaft 14 may alternatively be hollow or tubular. The distal tip 26 has the shape of an elliptical cone with the apex 34 of the cone disposed at the most distal point on the inner shaft 14. The apex 34 is pointed or sharpened so as to be able to penetrate skin and soft tissue. The elliptical base 36 of the cone is abuts the cutting head 28. The elliptical base 36 has substantially the same shape and circumferential extent as the outer surface 22 of the outer sheath 12. The distal tip 26 may have shapes other than an elliptical cone. For example, the distal tip 26 may transition from an elliptical shape at the base 36 to a shape that includes two or more flat surfaces. The distal tip 26 may thus have a diamond shape with four flat sides or edges when viewed in section taken perpendicular to or radially of the central longitudinal axis 32 at a location between the base 36 and the apex 34. As another alternative, the distal tip 26 may have two or more flat surfaces for the entire length of the distal tip.

The cutting head 28 of the inner shaft 14 is disposed between the distal tip 26 and the proximal connecting portion 30. The cutting head 28 has a distal end 38 and a proximal end 40. The distal end 38 of the cutting head 28 abuts and is connected to the elliptical base 36 of the distal tip 26. The proximal end 40 of the cutting head 28 abuts and is connected to the proximal connecting portion 30 of the inner shaft 14. The cutting head 28 has a length that extends between its distal end 38 and its proximal end 40. As best seen in FIG. 2, the cutting head 28 has an outer surface 42 with a generally elliptical shape when viewed in a cross-section taken radially or perpendicular to the central longitudinal axis 32 of the inner shaft 14. The outer surface 42 extends for the length of the cutting head 28, but is interrupted by two circumferentially spaced apart tissue-receiving surfaces 44.

Each tissue-receiving surface 44 is recessed from the outer surface 42 so as to define a depression for receiving a tissue sample, as described below. In addition, each tissue-receiving surface 44, when viewed in cross-section taken radially of or perpendicular to the central longitudinal axis 32 and the length of the inner shaft 14, has a first linear portion 46 extending along the major axis 48 of the elliptical shape of the outer surface 42. Further, each tissue receiving-surface 44, when viewed in cross-section taken radially or perpendicular to the length of the inner shaft 14, has a second linear portion 50 extending along the minor axis 52 of the elliptical shape of the outer surface 42. The first and second linear portions 46 and 50 are joined by a curved portion 54. At its radially outermost extent, the first linear portion 46 of the tissue-receiving surface 44 intersects a first portion 56 of the outer surface 42 to define a sharpened cutting edge 58. Similarly, at its radially outermost extent, the second linear portion 50 of the tissue-receiving surface 44 intersects a second portion 60 of the outer surface 42 to define a second edge 62. The second edge 62 is not sharpened and is not a cutting edge. The distance along the tissue-receiving surface 44 from the cutting edge 58 to the second edge 62 is the entire distance between the first and second portions 56 and 60 of the outer surface 42, which are spaced circumferentially apart from each other. The tissue-receiving surface 44 is a continuous surface free of any opening.

When the outer surface 42 of the inner shaft 14 is viewed in cross-section taken radially of or perpendicular to the central longitudinal axis 32 and the length of the inner shaft, each second portion 60 of the outer surface is (a) disposed circumferentially between the two first portions 56 of the outer surface and (b) separated circumferentially from the other second portion by each of the two first portions. In other words, the second portions 60 of the outer surface 42 are interposed circumferentially between the first portions 56 of the outer surface.

Figure 4:
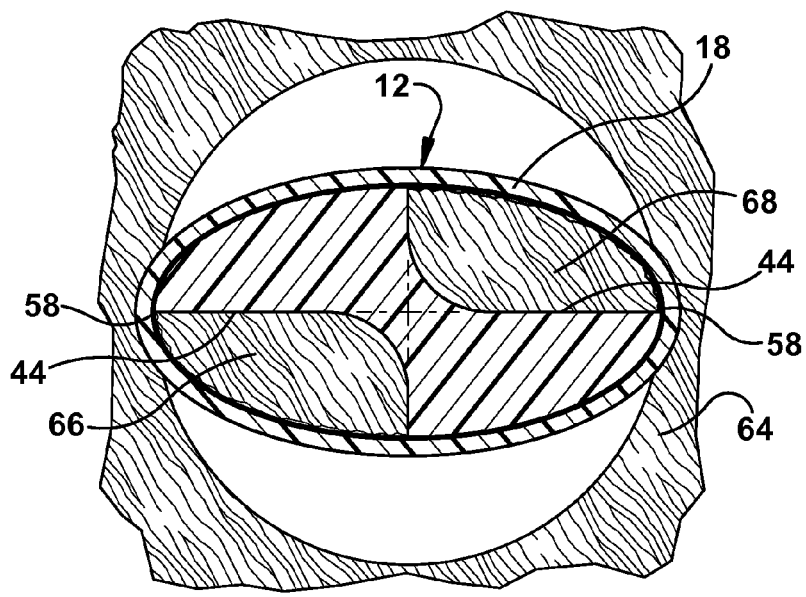
FIG. 4 is a view similar to FIG. 2 showing the tissue sampling device of FIG. 1 in a second step of collecting a tissue sample.

When assembled together, the cutting head 28 and the proximal connecting portion 30 of the inner shaft 14 are received within the tubular outer sheath 12. The proximal end (not shown) of the outer sheath 12 and the proximal connecting portion 30 of the inner shaft 14 are connected to a handle (not shown) or other mechanism that can be grasped by a user and that will permit necessary manipulation of the tissue sampling device 10. Such necessary manipulation of the tissue sampling device 10 includes being able to move the outer sheath 12 longitudinally relative to the inner shaft 14. More specifically, the tissue sampling device 10 has a closed condition and a fully open condition. In the fully open condition, which is illustrated in FIG. 1, the distal tip 26 and the cutting head 28 of the inner shaft 14 project axially or longitudinally beyond the open distal end 16 of the outer sheath 12. The tissue sampling device 10 also has multiple partially open conditions in which only a portion of the cutting head 28 of the inner shaft projects axially or longitudinally beyond the distal end 16 of the outer sheath 12. In either the fully open condition or a partially open condition, the cutting edges 58 of the cutting head 28 are thus exposed so as to be ready to sample tissue in a target area of the body. In the closed condition, which is illustrated in FIG. 4, the cutting head 28 of the inner shaft 14 is enclosed within the outer sheath 12. The distal tip 26 of the inner shaft 14 still projects axially or longitudinally beyond the open distal end 16 of the outer sheath 12, but the open distal end 16 of the outer shaft rests on the elliptical base 36 of the distal tip.

The necessary manipulation of the tissue sampling device 10 also includes being able to push the tissue sampling device so that the distal tip 26 of the inner shaft 14 will penetrate skin and/or other soft tissue. The necessary manipulation of the tissue sampling device 10 further includes being able to rotate the tissue sampling device around the central longitudinal axis 32 of the inner shaft 14 when the distal tip 26 has pierced the skin adjacent the target area of a human body and when the tissue sampling device is in its open condition with the cutting head 28 exposed.

In use, the tissue sampling device 10 is first placed in its closed condition with the pointed or sharpened distal tip 26 of the inner shaft 14 exposed. The distal tip 26 is pressed against a patient's skin adjacent to or overlying (i.e., lying or extending above and across) a target area of tissue. When the sharpened distal tip 26 pierces the skin, the tissue sampling device 10 is advanced into the patient's tissue until the cutting head 28 of the inner shaft 14 is positioned in the target area. The outer sheath 12 is then retracted or moved proximally relative to the inner shaft 14 until the cutting head 28 of the inner shaft is partially or fully exposed adjacent to tissue 64 of the target area. With the tissue sampling device 10 thus in an open condition, the tissue sampling device and the cutting head 28 of the inner shaft 14 are rotated about the central longitudinal axis 32 of the inner shaft 14, which is also the central longitudinal axis of the tissue sampling device. Because the tissue sampling device 10 and the cutting head 28 of inner shaft 14 both have an elliptical or generally elliptical shape in cross-section taken radially or perpendicular to the length of the outer sheath, rotation of the tissue sampling device and the cutting head causes the two cutting edges 58 of the cutting head to cut two tissue samples 66 and 68 (FIG. 3) from the tissue 64.

As the tissue sampling device 10 and the cutting head 28 of the inner shaft 14 are rotated, the two tissue samples 66 and 68 are sheared from the larger mass of tissue 64 and are moved onto the tissue-receiving surfaces 44 of the cutting head. After the tissue sampling device 10 and the cutting head 28 of the inner shaft 14 have been rotated through an arc of 180°, each of the cutting edges 58 reaches the point in the larger mass of tissue 64 from which the other tissue sample 68 or 66 has been cut. The outer sheath 12 is then advanced or moved distally relative to the inner shaft 14 so that that the sharpened distal end 16 of the outer sheath completely severs the two tissue samples 66 and 68 from the larger mass of tissue 64. The two tissue samples 66 and 68, which are separate from each other, are then both completely enclosed within the tissue sampling device 10. The tissue sampling device 10 is removed from the patient, and the two tissue samples 66 and 68 can be removed from the tissue sampling device for analysis.

FIGS. 5 and 6 illustrate a tissue sampling device 100, in accordance with a second example of the present invention. The tissue sampling device 100 includes a tubular outer sheath 112 and a coaxial inner shaft 114. The outer sheath 112 has a proximal end (not shown), a distal end 116, and a tubular body 118 extending between the proximal end and the distal end. The distal end 116 is sharpened to provide a cutting edge. The body 118 of the outer sheath 112 has an inner surface (not shown) and a substantially concentric outer surface 122. Both the inner surface (not shown) and the outer surface 122 extend the length of the outer sheath 112 between the distal end 116 and the proximal end (not shown). The outer sheath 112, including the inner surface and the outer surface 122 of the body 118 of the outer sheath, has an elliptical shape when viewed in a cross-section taken radially or perpendicular to the length of the outer sheath. The inner surface (not shown) defines a passage (not shown), which extends from the open distal end 116 of the outer sheath 112 to the proximal end (not shown). The outer sheath 112 may be fabricated from any suitable biocompatible material, such as titanium, stainless steel, plastic, ceramic or combinations of such materials.

The inner shaft 114 includes a pointed distal tip 126, a cutting head 128, and a proximal connecting portion 130. A central longitudinal axis 132 of the inner shaft 114 extends through the distal tip 126, the cutting head 128, and the proximal connecting portion 130. Except for the distal tip 126, the inner shaft 114 is a hollow, tubular member throughout its length, which extends in a direction along the central longitudinal axis 132. The inner shaft 114 may be fabricated from any suitable biocompatible material, such as titanium, stainless steel, plastic, ceramic or combinations of such materials, so long as the cutting head can be formed with sharpened edges, as explained below, for cutting tissue samples. The distal tip 126 has the shape of an elliptical cone with the apex 134 of the cone disposed at the most distal point on the inner shaft 114. The apex 134 is pointed or sharpened so as to be able to penetrate skin and soft tissue. The elliptical base 136 of the cone is adjacent the cutting head 128. The distal tip has a short elliptic cylinder portion 137 that extends from the elliptical base 136. The elliptic cylinder portion 137 abuts the cutting head 128 and has substantially the same shape and circumferential extent as the outer surface 122 of the outer sheath 112. Like the distal tip 26 of FIG. 1, the distal tip 126 may have shapes other than an elliptical cone.

The cutting head 128 of the inner shaft 114 is disposed between the distal tip 126 and the proximal connecting portion 130. The cutting head 128 is a hollow, tubular member and has a distal end 138 and a proximal end 140. The distal end 138 of the cutting head 128 abuts and is connected to the elliptic cylinder portion 137 of the distal tip 126. The proximal end 140 of the cutting head 128 abuts and is connected to the proximal connecting portion 130 of the inner shaft 114. The cutting head 128 has a length that extends between its distal end 138 and its proximal end 140. As best seen in FIG. 6, the cutting head 128 has an outer surface 142 with a generally elliptical shape when viewed in a cross-section taken radially or perpendicular to the central longitudinal axis 132 and the length of the inner shaft 114. The outer surface 142 extends for the length of the cutting head 128, but is interrupted by two circumferentially spaced gaps 143. The cutting head 128 also has an inner surface 144 that is generally parallel to the outer surface 142. Because of the gaps 143, the inner surface 144 is separated into two portions 145.

Each portion 145 of the inner surface 144 of the cutting head 128 is a tissue-receiving surface. Each tissue receiving surface 145 is, in effect, recessed from the outer surface 142 so as to define a depression for receiving a tissue sample, as described below. Along one longitudinally extending side, each tissue-receiving surface 145, when viewed in cross-section taken radially or perpendicular to the length and the central longitudinal axis 132 of the inner shaft 14, intersects a first portion 156 of the outer surface 142 to define a sharpened cutting edge 158 that extends in a straight line along the length of the inner shaft. Along its opposite longitudinally extending side, the tissue-receiving surface 145 intersects a narrow, radially extending surface 159 that extends between and joins the tissue-receiving surface 144 and the outer surface 142. The surface 159 is not sharpened nor are its intersections with the tissue-receiving surface 145 and the outer surface 142 sharpened. Neither the surface 159 nor either of the intersections defines a cutting edge.

The distance along the tissue-receiving surface 145 from the cutting edge 158 to the intersection between the tissue-receiving surface and the radially extending surface 159 is substantially greater than the distance across the radially extending surface from the intersection between the tissue-receiving surface and the radially extending surface to the intersection between the radially extending surface and the outer surface 142. Consequently, the distance along the tissue-receiving surface 145 constitutes a majority of the total distance between the cutting edge 158 and the intersection between the radially extending surface 159 and the outer surface 142, which intersection is adjacent to a second portion 160 of the outer surface that is spaced circumferentially apart from the first portion 156 adjacent the cutting edge 158. The tissue-receiving surface 145 is a continuous surface free of any opening.

Viewed in cross-section taken radially of or perpendicular to the central longitudinal axis 132 and the length of the inner shaft 114, the outer surface 142 of the inner shaft 114 has each second portion 160 of the outer surface (a) disposed circumferentially between the two first portions 156 of the outer surface and (b) separated circumferentially from the other second portion by each of the two first portions. In other words, the second portions 160 of the outer surface 142 are interposed circumferentially between the first portions 156 of the outer surface.

When assembled together, the cutting head 128 and the proximal connecting portion 130 of the inner shaft 114 are received within the tubular outer sheath 112. The proximal end (not shown) of the outer sheath 112 and the proximal connecting portion 130 of the inner shaft 114 are connected to a handle (not shown) or other mechanism that can be grasped by a user and that will permit necessary manipulation of the tissue sampling device 100. Such necessary manipulation of the tissue sampling device 100 includes being able to move the outer sheath 112 longitudinally relative to the inner shaft 114. More specifically, the tissue sampling device 100 has a closed condition and at least one open condition. In a fully open condition, which is illustrated in FIG. 5, the distal tip 126 and the cutting head 128 of the inner shaft 114 project axially or longitudinally beyond the open distal end 116 of the outer sheath 112. The tissue sampling device 100 also has multiple partially open conditions in which only a portion of the cutting head 128 of the inner shaft projects axially or longitudinally beyond the distal end 116 of the outer sheath 112. In either the fully open condition or a partially open condition, the cutting edges 158 of the cutting head 128 are thus exposed so as to be ready to sample tissue in a target area of the body. In the closed condition, which is not illustrated, the cutting head 128 of the inner shaft 114 is enclosed within the outer sheath 112. The distal tip 126 of the inner shaft 114 still projects axially or longitudinally beyond the open distal end 116 of the outer sheath 112, but the open distal end 116 of the outer shaft rests on the elliptic cylinder portion 137 of the distal tip.

The necessary manipulation of the tissue sampling device 100 also includes being able to push the tissue sampling device so that the distal tip 126 of the inner shaft 114 will penetrate skin and/or other soft tissue. The necessary manipulation of the tissue sampling device 100 further includes being able to rotate the tissue sampling device around the central longitudinal axis 132 of the inner shaft 114 when the distal tip 126 has pierced the skin adjacent the target area of a human body and when the tissue sampling device is in its open condition with the cutting head 128 exposed.

In use, the tissue sampling device 100 is first placed in its closed condition with the pointed or sharpened distal tip 126 of the inner shaft 114 exposed. The distal tip 126 is pressed against a patient's skin adjacent to or overlying (i.e., lying or extending above and across) a target area of tissue. When the sharpened distal tip 126 pierces the skin, the tissue sampling device 100 is advanced into the patient's tissue until the cutting head 128 of the inner shaft 114 is positioned in the target area. The outer sheath 112 is then retracted or moved proximally relative to the inner shaft 114 until the cutting head 128 of the inner shaft is exposed adjacent to tissue of the target area. With the tissue sampling device 100 thus in its open condition, the tissue sampling device and the cutting head 128 of the inner shaft 114 are rotated about the length of the inner shaft 114 and the central longitudinal axis 132, which is also the central longitudinal axis of the tissue sampling device. Because the tissue sampling device 100 and the cutting head 128 of inner shaft 114 both have an elliptical or generally elliptical shape in cross-section taken radially of or perpendicular to the central longitudinal axis 132 and the length of the inner shaft, rotation of the tissue sampling device and the cutting head causes the two cutting edges 158 of the cutting head to cut two tissue samples from the adjacent tissue.

As the tissue sampling device 100 and the cutting head 128 of inner shaft 114 are rotated, the two tissue samples are sheared from the larger mass of tissue and are moved onto the tissue-receiving surfaces 145 of the cutting head. After the tissue sampling device 100 and the cutting head 128 of the inner shaft 114 have been rotated through an arc of 180°, each of the cutting edges 158 reaches the point in the larger mass of tissue from which the other tissue sample has been cut. The outer sheath 112 is then advanced or moved distally relative to the inner shaft 114 so that that the sharpened distal end 116 of the outer sheath completely severs the two tissue samples from the larger mass of tissue. The two tissue samples, which are separate from each other, are then both completely enclosed within the tissue sampling device 100. The tissue sampling device 100 is removed from the patient, and the two tissue samples can be removed from the tissue sampling device for analysis.

FIGS. 7A through 7D illustrate a tissue sampling device 200, in accordance with a third example of the present invention. The tissue sampling device 200 includes a tubular outer sheath 212 and a coaxial inner shaft 214. The outer sheath 212 has a proximal end (not shown), a distal end 216, and a tubular body 218 extending between the proximal end and the distal end. The distal end 216 is sharpened to provide a cutting edge. The body 218 of the outer sheath 212 has an inner surface (not shown) and a substantially concentric outer surface 222. Both the inner surface (not shown) and the outer surface 222 extend the length of the outer sheath 212 between the distal end 216 and the proximal end (not shown). The outer sheath 212, including the inner surface and the outer surface 222 of the body 218 of the outer sheath, has a circular shape when viewed in a cross-section taken radially or perpendicular to the length of the outer sheath. The inner surface (not shown) defines a passage (not shown), which extends from the open distal end 216 of the outer sheath 212 to the proximal end (not shown). The outer sheath 212 may be fabricated from any suitable biocompatible material, such as titanium, stainless steel, plastic, ceramic or combinations of such materials.

The inner shaft 214 includes a cutting head 228 and a proximal connecting portion 230. A central longitudinal axis 232 of the inner shaft 214 extends through the cutting head 228 and the proximal connecting portion 230. The inner shaft 214 is a hollow, tubular member throughout most of its length, which extends in a direction along the central longitudinal axis 232. The inner shaft 214 may be fabricated from any suitable biocompatible material, such as titanium, stainless steel, plastic, ceramic or combinations of such materials, so long as the cutting head can be formed with sharpened edges, as explained below, for cutting tissue samples.

Figure 7A:
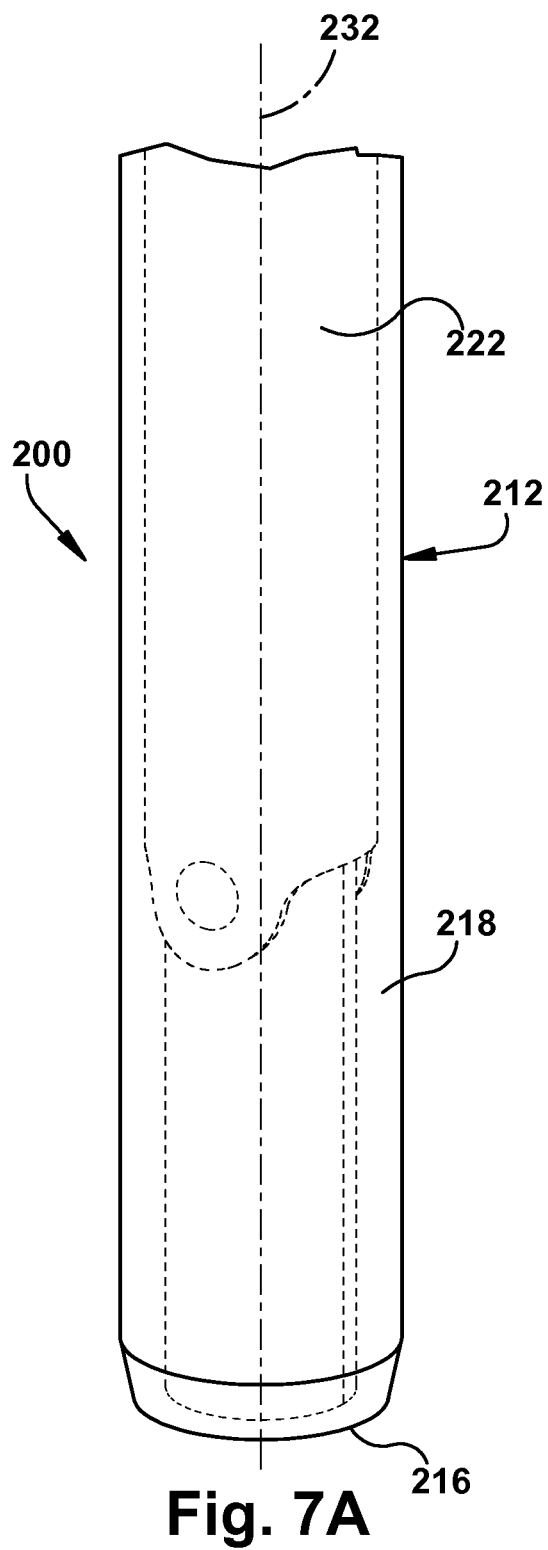
FIG. 7A is a perspective view of a tissue sampling device in accordance with a third embodiment of the present invention in a first stage of deployment.
Figure 7B:
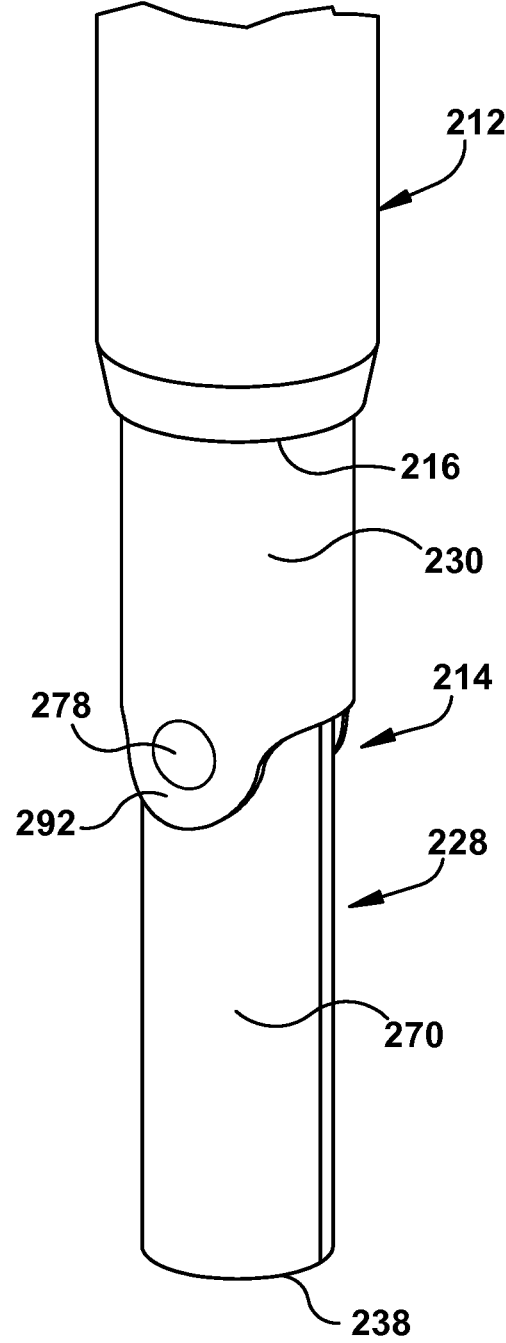
FIG. 7B is a perspective view of the tissue sampling device of FIG. 7A in a second stage of deployment.
Figure 7C:
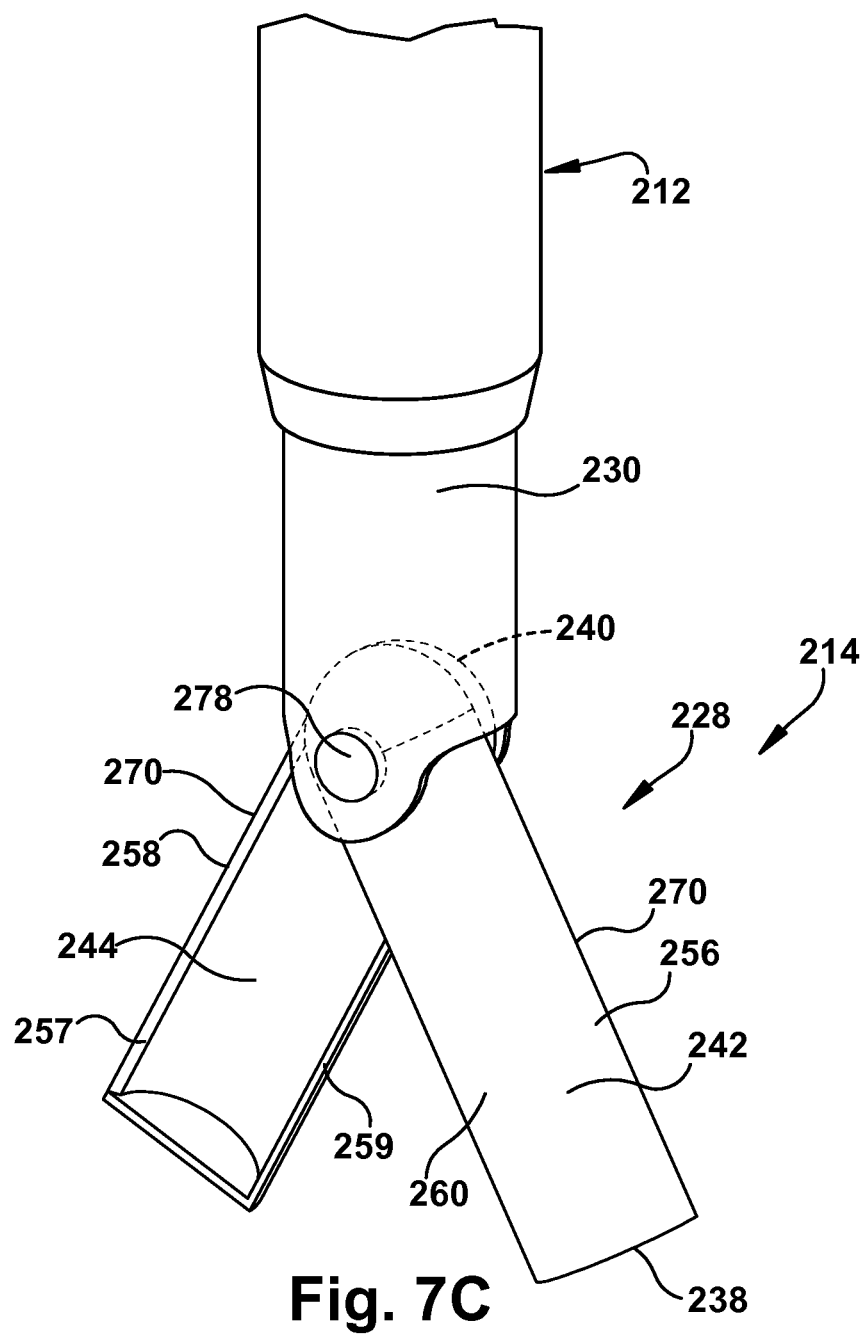
FIG. 7C is a perspective view of the tissue sampling device of FIG. 7A in a third stage of deployment.
Figure 7D:
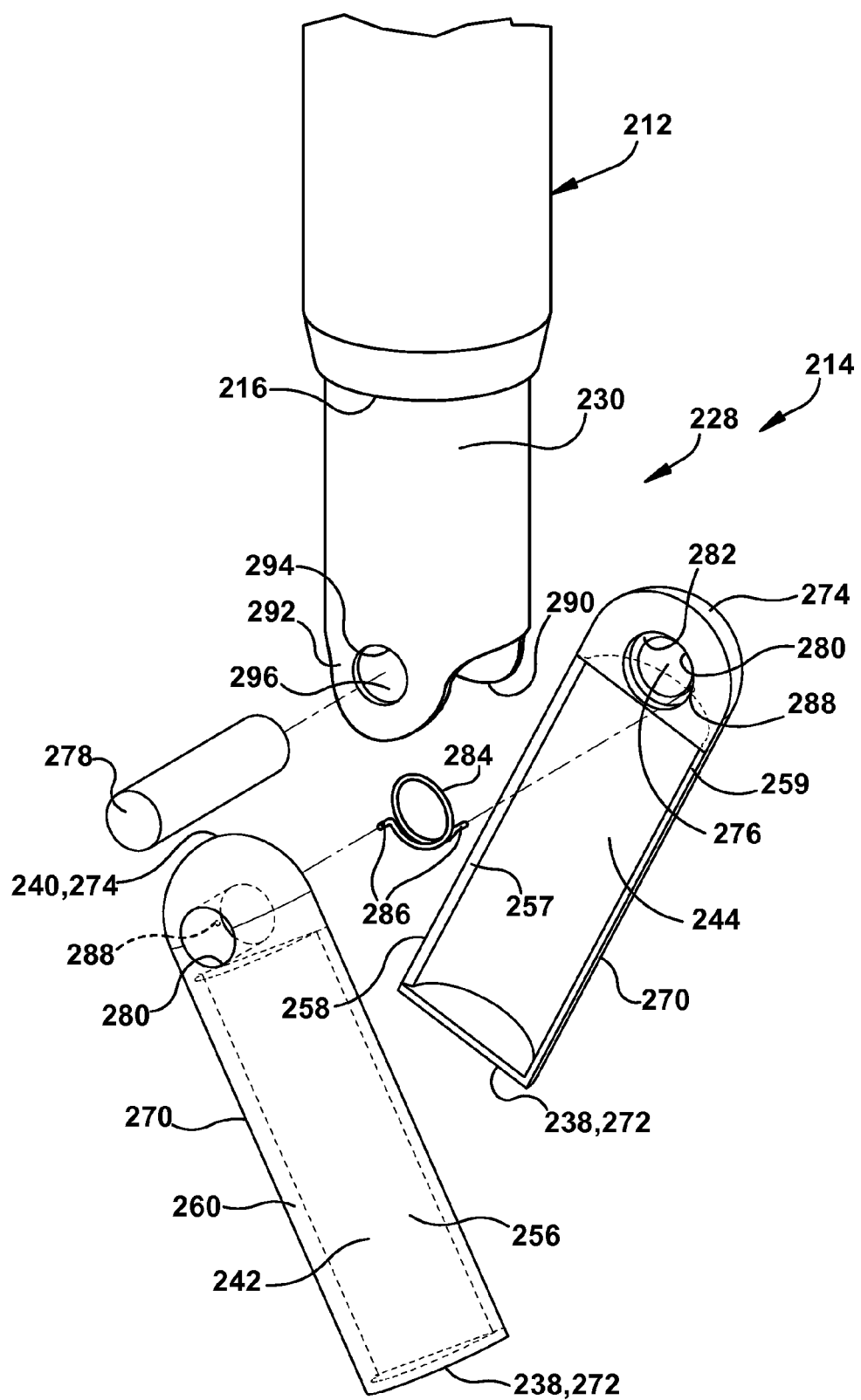
FIG. 7D is an exploded perspective view of the tissue sampling device of FIG. 7A in its third stage of deployment.

The cutting head 228 of the inner shaft 214 is disposed distally relative to the proximal connecting portion 230. The cutting head 228 is a generally hollow, tubular member and has a distal end 238 and a proximal end 240. The proximal end 240 of the cutting head 228 is overlapped by and is connected to the proximal connecting portion 230 of the inner shaft 214. The cutting head 228 has a length that extends between its distal end 238 and its proximal end 240. As best seen in FIGS. 7C and 7D, the cutting head 228 includes two scoops or half-cylinders 270. Each half-cylinder 270 has a closed distal end 272 that is coincident with the distal end 238 of the cutting head 228 and a closed proximal end 274 that is coincident with the proximal end 240 of the cutting head. Adjacent its proximal end 274, each half-cylinder 270 has a circular hole 276 that is configured and dimensioned to receive a cylindrical axle 278. The hole 276 is defined by an interior surface 280 of the half-cylinder 270. The interior surface 280 includes a radial step 282 that defines a recess that is larger in diameter than the hole 276 and the axle 278. The recess receives a circular spring 284. The circular spring 284 is configured and dimensioned to encircle the axle 278 and also has two oppositely directed stub end portions 286. The stub end portions 286 are configured and dimensioned to fit into two small holes 288 located adjacent the axle-receiving holes 276 in the half-cylinders 270.

Each half-cylinder 270 of the cutting head 228 has an outer surface 242 with a generally semi-circular shape when viewed in a cross-section taken radially or perpendicular to the central longitudinal axis 232 of the inner shaft 214. The outer surface 242 extends for the length of the cutting head 228. The cutting head 228 also has an inner surface 244 that is generally parallel to the outer surface 242. The inner surface 244 of each half-cylinder 270 of the cutting head 228 is a tissue-receiving surface. Each tissue-receiving surface 244 is, in effect, recessed from the outer surface 242 so as to define a depression for receiving a tissue sample, as described below. Along one longitudinally extending side, each tissue-receiving surface 244, when viewed in cross-section taken radially or perpendicular to the length and the central longitudinal axis 232 of the inner shaft 14, adjoins or intersects a narrow, angled surface 257 extending from a first portion 256 of the outer surface 242. This narrow, angled surface 257 intersects the first portion 256 of the outer surface 242 to define a sharpened cutting edge 258 that extends in a straight line lengthwise of the inner shaft 214. Along the opposite longitudinally extending side, the tissue-receiving surface 244 intersects a narrow, radially extending surface 259 that extends between and joins the tissue-receiving surface 244 and the outer surface 242. The surface 259 is not sharpened nor are its intersections with the tissue-receiving surface 244 and the outer surface 242 sharpened. Neither the surface 259 nor either of the intersections defines a cutting edge.

The distance along the tissue-receiving surface 244 from its intersection with the narrow, angled surface 257 to the intersection between the tissue-receiving surface and the narrow, radially extending surface 259 is substantially greater than the combined distances across the narrow, angled surface and the narrow, radially extending surface. Consequently, the distance along the tissue-receiving surface 244 constitutes a majority of the total distance between the cutting edge 258 and the intersection between the radially extending surface 259 and the outer surface 242, which intersection is adjacent to a second portion 260 of the outer surface that is spaced circumferentially apart from the first portion 256 adjacent the cutting edge 258. The tissue-receiving surface 244 is a continuous surface free of any opening.

The proximal connecting portion 230 of the inner shaft 214 is tubular or hollow and includes an open distal end 290. The inner surface (not shown) of the proximal connecting portion 230 defines an inner passage (not shown) that is shaped and dimensioned to receive the cutting head 228. The distal end 290 of the proximal connecting portion 230 is configured to provide two ears or lugs 292 adjacent to and on opposed sides of the distal end of the proximal connecting portion. Each lug 292 includes a surface 294 that defines a circular hole 296. Each circular hole 296 is shaped and dimensioned to receive and fit closely around the axle 278.

When the outer surface 242 of the inner shaft 214 is viewed in cross-section taken radially of or perpendicular to the central longitudinal axis 232 and the length of the inner shaft, each second portion 260 of the outer surface is (a) disposed circumferentially between the two first portions 256 of the outer surface and (b) separated circumferentially from the other second portion by each of the two first portions. In other words, the second portions 260 of the outer surface 242 are interposed circumferentially between the first portions 256 of the outer surface.

To assemble the cutting head 228 with the proximal connection portion 230, the circular spring 284 is placed in the recess defined by the radial step 282 in the surface 280 of each half-cylinder. At the same time, the stub end portions 286 of the circular spring 284 are inserted into the small holes 288 adjacent the axle-receiving holes 276 in the half-cylinders 270. The two half-cylinders 270 are then positioned so that their proximal ends 274 are disposed between the lugs 292 of the proximal connecting portion 230 with the holes 276 aligned with the holes 296. The axle 278 is pushed into the hole 296 in one of the lugs 292, through the holes 276 in the half-cylinders and through the open center of the circular spring 284, and into the hole 296 in the opposite lug 292. The axle 278 fits tightly within the holes 296 so that the axle will be retained in the lugs 292. The axle 278 will fit more loosely in the holes 276 in the half-cylinders 270 so that the half-cylinders can pivot on the axle. The spring 284 will cause the two half-cylinders 270 to pivot away from each other into the position shown in FIG. 7C.

When assembled together, the cutting head 228 and the proximal connecting portion 230 of the inner shaft 214 are received within the tubular outer sheath 212. The proximal end (not shown) of the outer sheath 212 and the proximal connecting portion 230 of the inner shaft 214 are connected to a handle (not shown) or other mechanism that can be grasped by a user and that will permit necessary manipulation of the tissue sampling device 200. Such necessary manipulation of the tissue sampling device 200 includes being able to move the outer sheath 212 longitudinally relative to the inner shaft 214. More specifically, the tissue sampling device 200 has a closed condition and a fully open condition. In the fully open condition, which is illustrated in FIG. 7C, the cutting head 228 of the inner shaft 214 projects axially or longitudinally beyond the open distal end 216 of the outer sheath 212. The tissue sampling device 200 also has multiple partially open conditions in which only a portion of the cutting head 228 of the inner shaft 214 projects axially or longitudinally beyond the distal end 216 of the outer sheath 212. In either the fully open condition or a partially open condition, the spring 284 causes the two half-cylinders 270 of the cutting head 228 to pivot away from each other. The cutting edges 258 of the cutting head 228 are thus exposed so as to be ready to sample tissue in a target area of the body. In the closed condition, which is illustrated in FIG. 7A, the cutting head 228 of the inner shaft 214 is enclosed within the outer sheath 212. The open distal end 216 of the outer sheath 212 projects beyond the distal end 238 of the cutting head 228 and beyond the distal ends 272 of the half-cylinders.

The necessary manipulation of the tissue sampling device 200 also includes being able to push the tissue sampling device so that the distal end 216 of the outer sheath 212 will penetrate skin and/or other soft tissue. Penetration of the skin can be facilitated by forming the distal ends 272 of the half-cylinders with optional pointed and sharpened tips (not shown). The necessary manipulation of the tissue sampling device 200 further includes being able to rotate the tissue sampling device around the central longitudinal axis 232 of the inner shaft 114 when the distal end 216 of the outer sheath 212 has pierced the skin adjacent the target area of a human body and when the tissue sampling device is in its open condition with the cutting head 228 exposed.

In use, the tissue sampling device 200 is first placed in its closed condition with the pointed or sharpened distal end 216 of the outer sheath 212 exposed beyond the distal end 238 of the cutting head 228. The distal end 216 of the outer sheath 212 is pressed against a patient's skin adjacent to or overlying (i.e., lying or extending above and across) a target area of tissue. When the sharpened distal end 216 of the outer sheath 212 pierces the skin, the tissue sampling device 200 is advanced into the patient's tissue until the cutting head 228 of the inner shaft 214 is positioned in the target area. The outer sheath 212 is then retracted or moved proximally relative to the inner shaft 214 until at least a portion of the cutting head 228 of the inner shaft is exposed adjacent to tissue of the target area. Retraction of the outer sheath 212 allows the spring 284 to bias or force the two half-cylinders 270 to pivot or rotate away from each other, ultimately reaching the position shown in FIG. 7C. With the tissue sampling device 200 in an open condition, the tissue sampling device and the cutting head 228 of the inner shaft 214 are rotated about the length of the inner shaft 214 and about the central longitudinal axis 232, which is also the central longitudinal axis of the tissue sampling device. Rotation of the tissue sampling device 200 and the cutting head 228 causes the two cutting edges 258 of the cutting head to cut two tissue samples from the adjacent tissue. Such rotation of the tissue sampling device 200 may be accompanied by simultaneous retraction of the outer sheath 212 so that increasing lengths of the two cutting edges 258 are exposed as the tissue sampling device is rotated.

As the tissue sampling device 200 and the cutting head 228 of inner shaft 214 are rotated, the two tissue samples are sheared from the larger mass of tissue and are moved onto the tissue-receiving surfaces 244 of the cutting head. After the tissue sampling device 200 and the cutting head 228 of the inner shaft 214 have been rotated through an arc of 180°, each of the cutting edges 258 reaches the point in the larger mass of tissue from which the other tissue sample has been cut. The outer sheath 212 is then advanced or moved distally relative to the inner shaft 214 so that that the sharpened distal end 216 of the outer sheath forces the two half-cylinders 270 into a closed position facing each other and aligned with each other and also ensures that the two tissue samples are completely severed from the larger mass of tissue. The two tissue samples, which are separate from each other, are then both completely enclosed within the tissue sampling device 200. The tissue sampling device 200 is removed from the patient, and the two tissue samples can be removed from the tissue sampling device for analysis.

The tissue sampling device 200 of FIGS. 7A through 7D embodies one example mechanism for implementing the operation of two half-cylinders 270 to cut tissue samples from a large mass of tissue. FIGS. 8 and 9 illustrate another example mechanism for implementing the operation of two such half-cylinders. The tissue sampling device 300 of FIGS. 8 and 9 incorporates many structural elements that are substantially similar to elements of the tissue sampling device 200 of FIGS. 7A-7D. Similar structural elements are given the same reference numerals as the corresponding structural elements of FIGS. 7A-7D, but increased by 100.

In the tissue sampling device 300 of FIGS. 8 and 9, the single spring 284 of the tissue sampling device 200 is eliminated and replaced with two springs 384a and 384b that connect two scoops or half cylinders 370a and 370b, respectively, to the proximal connecting portion 330. Like the spring 284, the springs 384a and 384b bias the half-cylinders 370a and 370b away from each other so that the cutting edge 358 on each half-cylinder 370a, 370b is exposed to adjacent tissue. The springs 384a and 384b also replace the axle 278 in that each of the springs is flexible enough to bend and allow movement of its associated half-cylinder 370a, 370b without the need for an axle. Further, the springs 384a and 384b are positioned adjacent the outer circumference and the outer surface 342 of each half-cylinder 370a, 370b so that the distal end 316 of the outer sheath 312 can move or ride along the surface of each spring to force the two half-cylinders and the cutting head back into a closed position.

Like the half-cylinders 270 of the tissue sampling device of FIGS. 7A-7D, each half-cylinder 370a, 370b has a closed distal end 372 that is coincident with the distal end 338 of the cutting head 328 and a closed proximal end 374 that is coincident with the proximal end 340 of the cutting head. Adjacent its proximal end 374, each half-cylinder 370a, 370b is joined to its associated spring 384a, 384b. Each spring 384a, 384b, which is a leaf spring, is joined in turn to the tubular or hollow proximal connecting portion 330 of the inner shaft 314. Each half-cylinder 370a, 370b of the cutting head 228 has an outer surface 342 with a generally semi-circular shape when viewed in a cross-section taken radially or perpendicular to the central longitudinal axis 332 of the inner shaft 314. The outer surface 342 extends for the length of the cutting head 328. The cutting head 328 also has an inner surface 344 that is generally parallel to the outer surface 342. The inner surface 344 of each half-cylinder 370a, 370b of the cutting head 328 is a tissue-receiving surface. Each tissue-receiving surface 344 is, in effect, recessed from the outer surface 342 so as to define a depression for receiving a tissue sample, as described below. Along one longitudinally extending side, each tissue-receiving surface 344, when viewed in cross-section taken radially or perpendicular to the central longitudinal axis 332 of the inner shaft 314, adjoins or intersects a narrow, angled surface 357 extending from a first portion 356 of the outer surface 342. This narrow, angled surface 357 intersects the first portion 356 of the outer surface 342 to define a sharpened cutting edge 358 that extends in a straight line lengthwise of the inner shaft 314. Along the opposite longitudinally extending side, the tissue-receiving surface 344 intersects a narrow, radially extending surface 359 that extends between and joins the tissue-receiving surface 344 and the outer surface 342. The surface 359 is not sharpened nor are its intersections with the tissue-receiving surface 344 and the outer surface 342 sharpened. Neither the surface 359 nor either of the intersections defines a cutting edge.

The distance along the tissue-receiving surface 344 from its intersection with the narrow, angled surface 357 to the intersection between the tissue-receiving surface 344 and the narrow, radially extending surface 359 is substantially greater than the combined distances across the narrow, angled surface and across the narrow, radially extending surface. Consequently, the distance along the tissue-receiving surface 344 constitutes a majority of the total distance between the cutting edge 358 and the intersection between the radially extending surface 359 and the outer surface 342, which intersection is adjacent to a second portion 360 of the outer surface that is spaced circumferentially apart from the first portion 356 adjacent the cutting edge 358. The tissue-receiving surface 344 is a continuous surface free of any opening When the outer surface 342 of the inner shaft 314 is viewed in cross-section taken radially of or perpendicular to the central longitudinal axis 332 and the length of the inner shaft, each second portion 360 of the outer surface is (a) disposed circumferentially between the two first portions 356 of the outer surface and (b) separated circumferentially from the other second portion by each of the two first portions. In other words, the second portions 360 of the outer surface 342 are interposed circumferentially between the first portions 356 of the outer surface.

In use, the tissue sampling device 300 is operated and functions like the tissue sampling device 200 of FIGS. 7A-7D. The sharpened distal end 316 of the outer sheath 312 is pressed against a patient's skin adjacent to or overlying (i.e., lying or extending above and across) a target area of tissue. When the sharpened distal end 316 of the outer sheath 312 pierces the skin, the tissue sampling device 300 is advanced into the patient's tissue until the cutting head 328 of the inner shaft 314 is positioned in the target area. Penetration of the skin can be facilitated by forming the distal ends 372a and 372b of the half-cylinders 370a and 370b with optional pointed and sharpened tips (not shown). The outer sheath 312 is then retracted or moved proximally relative to the inner shaft 314 until at least a portion of the cutting head 328 of the inner shaft is exposed adjacent to tissue of the target area. Retraction of the outer sheath 312 allows the springs 384a and 384b to bias or force the two half-cylinders 370a and 370b to pivot or move away from each other, ultimately reaching the position shown in FIG. 9. With the tissue sampling device 300 in an open condition, the tissue sampling device and the cutting head 328 of the inner shaft 314 are rotated about the central longitudinal axis 332 of the inner shaft 314, which is also the central longitudinal axis of the tissue sampling device. Rotation of the tissue sampling device 300 and the cutting head 328 causes the two cutting edges 358 of the cutting head to cut two tissue samples from the adjacent tissue. Such rotation of the tissue sampling device 300 may be accompanied by simultaneous retraction of the outer sheath 312 so that increasing lengths of the two cutting edges 358 are exposed as the tissue sampling device is rotated.

As the tissue sampling device 300 and the cutting head 328 of inner shaft 314 are rotated, the two tissue samples are sheared from the larger mass of tissue and are moved onto the tissue-receiving surfaces 344 of the cutting head. After the tissue sampling device 300 and the cutting head 328 of the inner shaft 314 have been rotated through an arc of 180°, each of the cutting edges 358 reaches the point in the larger mass of tissue from which the other tissue sample has been cut. The outer sheath 312 is then advanced or moved distally relative to the inner shaft 314 so that that the sharpened distal end 316 of the outer sheath forces the two half-cylinders 370a, 370b into a closed position facing each other and aligned with each other and also ensures that the two tissue samples are completely severed from the larger mass of tissue. The two tissue samples, which are separate from each other, are then both completely enclosed within the tissue sampling device 300. The tissue sampling device 300 is removed from the patient, and the two tissue samples can be removed from the tissue sampling device for analysis.

FIGS. 10 and 11 illustrate a third example mechanism for implementing the operation of two half-cylinders. The tissue sampling device 400 of FIGS. 10 and 11 incorporates many structural elements that are substantially similar to elements of the tissue sampling device 200 of FIGS. 7A-7D. Similar structural elements are given the same reference numerals as the corresponding structural elements of FIGS. 7A-7D, but increased by 200.

In the tissue sampling device 400 of FIGS. 10 and 11, the spring 284 of the tissue sampling device 200 is eliminated. In its place, a longitudinally movable central post 497 causes the scoops or half-cylinders 470a and 470b to pivot or rotate away from each other so that the cutting edge 458 on each half-cylinder 470a, 470b is exposed to adjacent tissue. Like the half-cylinders 270 of the tissue sampling device of FIGS. 7A-7D, each half-cylinder 470a, 470b has a closed distal end 472 that is coincident with the distal end 438 of the cutting head 428 and a closed proximal end 474 that is coincident with the proximal end 440 of the cutting head. Adjacent its proximal end 474, each half-cylinder 470a, 470b is joined to the proximal connecting portion 430 of the inner shaft 414 via an axle 478. The proximal end 474 of each half-cylinder 470a, 470b is formed with an inclined surface 475 that receives a narrow distal end portion 498 of the central post 497.

Each half-cylinder 470a, 470b of the cutting head 428 has an outer surface 442 with a generally semi-circular shape when viewed in a cross-section taken radially or perpendicular to the length and the central longitudinal axis 432 of the inner shaft 414. The outer surface 442 extends for the length of the cutting head 428. The cutting head 428 also has an inner surface 444 that is generally parallel to the outer surface 442. The inner surface 444 of each half-cylinder 470a, 470b of the cutting head 428 is a tissue-receiving surface. Each tissue-receiving surface 444 is, in effect, recessed from the outer surface 442 so as to define a depression for receiving a tissue sample, as described below. Along one longitudinally extending side, each tissue receiving surface 444, when viewed in cross-section taken radially or perpendicular to the length and the central longitudinal axis 432 of the inner shaft 414, adjoins or intersects a narrow, angled surface 457 extending from a first portion 456 of the outer surface 442. This narrow, angled surface 457 intersects the first portion 456 of the outer surface 442 to define a sharpened cutting edge 458 that extends in a straight line lengthwise of the inner shaft 414. Along the opposite longitudinally extending side, the tissue-receiving surface 444 intersects a narrow, radially extending surface 459 that extends between and joins the tissue-receiving surface 444 and the outer surface 442. The surface 459 is not sharpened nor are its intersections with the tissue-receiving surface 444 and the outer surface 442 sharpened. Neither the surface 459 nor either of the intersections defines a cutting edge.

The distance along the tissue-receiving surface 444 from its intersection with the narrow, angled surface to the intersection between the tissue-receiving surface 444 and the narrow, radially extending surface 459 is substantially greater than the combined distances across the narrow, angled surface 457 and across the narrow, radially extending surface 459. Consequently, the distance along the tissue-receiving surface 344 constitutes a majority of the total distance between the cutting edge 458 and the intersection between the radially extending surface 459 and the outer surface 442, which intersection is adjacent to a second portion 460 of the outer surface that is spaced circumferentially apart from the first portion 456 adjacent the cutting edge 458. The tissue-receiving surface 344 is a continuous surface free of any opening.

When the outer surface 442 of the inner shaft 414 is viewed in cross-section taken radially of or perpendicular to the central longitudinal axis 432 and the length of the inner shaft, each second portion 460 of the outer surface is (a) disposed circumferentially between the two first portions 456 of the outer surface and (b) separated circumferentially from the other second portion by each of the two first portions. In other words, the second portions 460 of the outer surface 442 are interposed circumferentially between the first portions 456 of the outer surface.

In use, the tissue sampling device 400 is operated and functions in a manner similar to the tissue sampling device 200 of FIGS. 7A-7D. The sharpened distal end 416 of the outer sheath 412 is pressed against a patient's skin adjacent to or overlying (i.e., lying or extending above and across) a target area of tissue. When the sharpened distal end 416 of the outer sheath 412 pierces the skin, the tissue sampling device 400 is advanced into the patient's tissue until the cutting head 428 of the inner shaft 414 is positioned in the target area. Penetration of the skin can be facilitated by forming the distal ends 472a and 472b of the half-cylinders 470a and 470b with optional pointed and sharpened tips (not shown). The outer sheath 412 is then retracted or moved proximally relative to the inner shaft 414 until the cutting head 428 of the inner shaft is exposed adjacent to tissue of the target area. The central post 497 is moved distally relative to the tubular inner shaft 414 so that the narrow distal end portion 498 of the central post presses on the inclined surfaces 475 on the proximal ends of the half-cylinders 470a, 470b to bias or force the two half-cylinders to pivot or rotate away from each other into the position shown in FIG. 11. With the tissue sampling device 400 thus in its open condition, the tissue sampling device and the cutting head 428 of the inner shaft 414 are rotated about the length of the inner shaft 414 and about the central longitudinal axis 432 of the inner shaft 414, which is also the central longitudinal axis of the tissue sampling device. Rotation of the tissue sampling device 400 and the cutting head 428 causes the two cutting edges 458 of the cutting head to cut two tissue samples from the adjacent tissue.

As the tissue sampling device 400 and the cutting head 428 of inner shaft 414 are rotated, the two tissue samples are sheared from the larger mass of tissue and are moved onto the tissue-receiving surfaces 444 of the cutting head. After the tissue sampling device 400 and the cutting head 428 of the inner shaft 414 have been rotated through an arc of 180°, each of the cutting edges 458 reaches the point in the larger mass of tissue from which the other tissue sample has been cut. The central post 497 is then moved proximally relative to the inner shaft 414 and the outer sheath 412 is advanced or moved distally relative to the inner shaft 414 so that that the sharpened distal end 416 of the outer sheath forces the two half-cylinders 470a, 470b into a closed position facing each other and aligned with each other and also ensures that the two tissue samples are completely severed from the larger mass of tissue. The two tissue samples, which are separate from each other, are then both completely enclosed within the tissue sampling device 400. The tissue sampling device 400 is removed from the patient, and the two tissue samples can be removed from the tissue sampling device for analysis.

Figure 12:
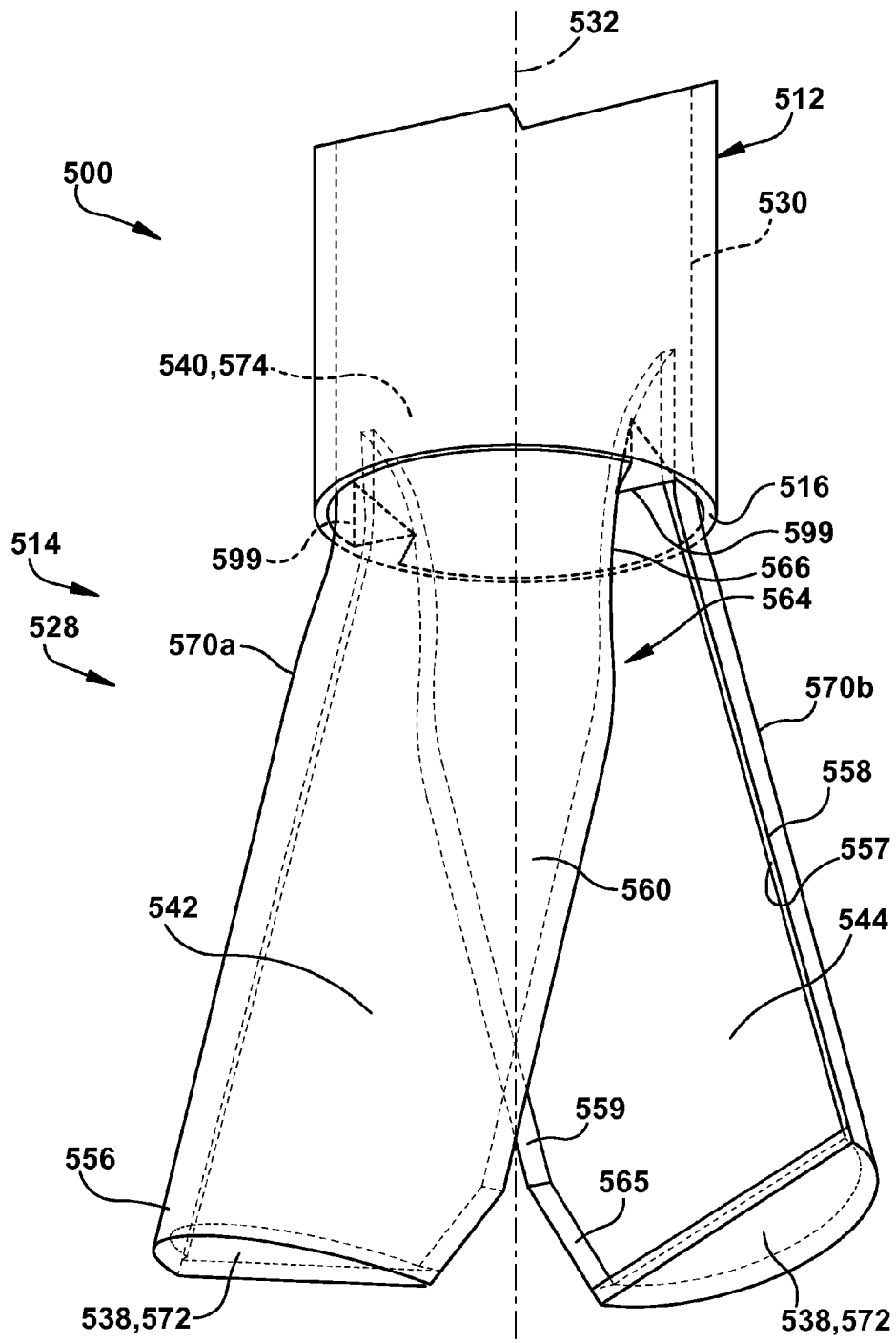
FIG. 12 is a perspective view of a tissue sampling device in accordance with a sixth embodiment of the present invention when fully deployed.

FIG. 12 illustrates a fourth example mechanism for implementing the operation of two half-cylinders. The tissue sampling device 500 of FIG. 12 incorporates many structural elements that are substantially similar to elements of the tissue sampling device 200 of FIGS. 7A-7D. Similar structural elements are given the same reference numerals as the corresponding structural elements of FIGS. 7A-7D, but increased by 300.

In the tissue sampling device 500 of FIG. 12, the spring 284 of the tissue sampling device 200 is eliminated. In its place, the scoops or half-cylinders 570a and 570b are formed in one piece with the proximal connecting portion 530 of the tubular or hollow inner shaft 514. Diametrically-extending wedge elements or wedges 599 are connected to diametrically opposite portions of the outer sheath 512. The wedges 599 are used to force the two half-cylinders 570a, 570b away from each other so that the cutting edge 558 on each half-cylinder is exposed to adjacent tissue. Like the half-cylinders 270 of the tissue sampling device of FIGS. 7A-7D, each half-cylinder 570a, 570b has a closed distal end 572 that is coincident with the distal end 538 of the cutting head 528 and a closed proximal end 574 that is coincident with the proximal end 540 of the cutting head. At its proximal end 574, each half-cylinder 570a, 570b is joined to the proximal connecting portion 530 of the inner shaft 514 by being formed in one piece with the proximal connecting portion. The proximal ends 574 of the half-cylinders 570a, 570b also merge with each other. More specifically, each half-cylinder 570a, 570b is separated from the other half-cylinder by two slots 564 formed at diametrically opposite locations on the tubular inner shaft 514. Each slot 564 is defined by and between the sharpened cutting edge 558 of one half-cylinder 570a, 570b and the narrow, radially extending surface 559 of the other half-cylinder. For a majority of its length, each slot 564 has a constant width. At the distal end 538 of the cutting head 528, however, each radially extending surface 559 is formed with a surface portion 565 that is inclined away from the adjacent cutting edge 558 and that provides a space to receive a wedge 599. Also, adjacent the proximal end 540 of the cutting head 528, the radially extending surface 559 is formed with a surface portion 566 that curves away from the adjacent cutting edge 558 and that provides stress relief to allow additional flexing of the half-cylinders 570a, 570b.

Each half-cylinder 570a, 570b of the cutting head 528 has an outer surface 542 with a generally semi-circular shape when viewed in a cross-section taken radially or perpendicular to the central longitudinal axis 532 of the inner shaft 514. The outer surface 542 extends for the length of the cutting head 528. The cutting head 528 also has an inner surface 544 that is generally parallel to the outer surface 542. The inner surface 544 of each half-cylinder 570a, 570b of the cutting head 528 is a tissue-receiving surface. Each tissue-receiving surface 544 is, in effect, recessed from the outer surface 542 so as to define a depression for receiving a tissue sample, as described below. Along one longitudinally extending side, each tissue receiving surface 544, when viewed in a cross-section taken radially or perpendicular to the length and the central longitudinal axis 532 of the inner shaft 514, adjoins or intersects a narrow, angled surface 557 extending from a first portion 556 of the outer surface 542. This narrow, angled surface 557 intersects the first portion 556 of the outer surface 542 to define a sharpened cutting edge 558 that extends in a straight line lengthwise of the inner shaft 514. Along the opposite longitudinally extending side, the tissue-receiving surface 544 intersects a narrow, radially extending surface 559 that extends between and joins the tissue-receiving surface 544 and the outer surface 542. The radially extending surface 559 is not sharpened nor are its intersections with the tissue-receiving surface 544 and the outer surface 542 sharpened. Neither the surface 559 nor either of the intersections defines a cutting edge.

The distance along the tissue-receiving surface 544 from its intersection with the narrow, angled surface 557 to the intersection between the tissue-receiving surface 544 and the narrow, radially extending surface 559 is substantially greater than the combined distances across the narrow, angled surface and across the narrow, radially extending surface 559. Consequently, the distance along the tissue-receiving surface constitutes a majority of the total distance between the cutting edge 558 and the intersection between the radially extending surface 559 and the outer surface 542, which intersection is adjacent to a second portion 560 of the outer surface that is spaced circumferentially apart from the first portion 556 adjacent the cutting edge 558. The tissue-receiving surface 544 is a continuous surface free of any opening When the outer surface 542 of the inner shaft 514 is viewed in cross-section taken radially of or perpendicular to the central longitudinal axis 532 and the length of the inner shaft, each second portion 560 of the outer surface is (a) disposed circumferentially between the two first portions 556 of the outer surface and (b) separated circumferentially from the other second portion by each of the two first portions. In other words, the second portions 560 of the outer surface 542 are interposed circumferentially between the first portions 556 of the outer surface.

In use, the tissue sampling device 500 is operated and functions in a manner similar to the tissue sampling device 200 of FIGS. 7A-7D. The tissue sampling device 500 is first placed in its closed condition (not shown) with the outer sheath 512 positioned adjacent the distal end 538 of the cutting head 528 and the wedges 599 in the spaces provided by the inclined surface portions 565. In the closed condition, the two half-cylinders 570a, 570b face each other and are aligned with each other. The sharpened distal end 516 of the outer sheath 512 is then pressed against a patient's skin adjacent to or overlying (i.e., lying or extending above and across) a target area of tissue. When the sharpened distal end 516 of the outer sheath 512 pierces the skin, the tissue sampling device 500 is advanced into the patient's tissue until the cutting head 528 of the inner shaft 514 is positioned in the target area. Penetration of the skin can be facilitated by forming the distal ends 572a and 572b of the half-cylinders 570a and 570b with optional pointed and sharpened tips (not shown). The outer sheath 512 is then retracted or moved proximally relative to the inner shaft 514. The proximal movement of the outer sheath 512 moves the wedge 599 out of the spaces provided by the inclined surface portions 565 and into the more narrow major parts of the slots 564. As the wedges 599 move into the more narrow parts of the slots 564, the wedges tend to force the two half-cylinders 570a, 570b apart from one another. The stress relief provided by the curved surface portion 566, which is disposed along only one edge of each half-cylinder 570a, 570b, allows the half-cylinders to twist or move in more of a side-to-side motion, like the pivoting motion of the half-cylinders 270, 370a, 370b, 470a, and 470b, rather than moving directly away from one another in a flapping motion. The proximal movement of the wedges 599 thus biases or forces the two half-cylinders 570a, 570b to pivot or rotate away from each other into the position shown in FIG. 12. With the tissue sampling device 500 thus in its open condition, the tissue sampling device and the cutting head 528 of the inner shaft 514 are rotated about the length of the inner shaft 514 and about the central longitudinal axis 532 of the inner shaft 514, which is also the central longitudinal axis of the tissue sampling device. Rotation of the tissue sampling device 500 and the cutting head 528 causes the two cutting edges 558 of the cutting head to cut two tissue samples from the adjacent tissue.

As the tissue sampling device 500 and the cutting head 528 of inner shaft 514 are rotated, the two tissue samples are sheared from the larger mass of tissue and are moved onto the tissue-receiving surfaces 544 of the cutting head. After the tissue sampling device 500 and the cutting head 528 of the inner shaft 514 have been rotated through an arc of 180°, each of the cutting edges 558 reaches the point in the larger mass of tissue from which the other tissue sample has been cut. The outer sheath 512 is then moved distally relative to the inner shaft 514 so that that the sharpened distal end 516 of the outer sheath forces the two half-cylinders 570a, 570b into a closed position facing each other and aligned with each other and also ensures that the two tissue samples are completely severed from the larger mass of tissue. The two tissue samples, which are separate from each other, are then both completely enclosed within the tissue sampling device 500. The tissue sampling device 500 is removed from the patient, and the two tissue samples can be removed from the tissue sampling device for analysis.

FIGS. 13 and 14 illustrate a fifth example mechanism for implementing the operation of two scoops or half-cylinders. The tissue sampling device 600 of FIGS. 13 and 14 incorporates many structural elements that are substantially similar to elements of the tissue sampling device 200 of FIGS. 7A-7D. Similar structural elements are given the same reference numerals as the corresponding structural elements of FIGS. 7A-7D, but increased by 400.

In the tissue sampling device 600 of FIGS. 13 and 14, the pivoting motion of the half-cylinders 270 is replaced with sliding motion. Like the half-cylinders 270 of the tissue sampling device of FIGS. 7A-7D, each scoop or half-cylinder 670a, 670b of the cutting head 628 of the tissue sampling device 600 has a closed distal end 672 that is coincident with the distal end 638 of the cutting head and a closed proximal end 674a, 674b that is coincident with the proximal end 640 of the cutting head. At its proximal end 674a, 674b, each half-cylinder 670a, 670b is joined to the proximal connecting portion (not shown) of the inner shaft 614. The proximal ends 674a and 674b of the half-cylinders 670a and 670b, respectively, are formed with proximally extending posts 664a and 664b. The posts 664a and 664b are positioned approximately mid-way across the diametrically-extending edges of the corresponding proximal ends 674a and 674b. The posts 664a and 664b may be connected to the proximal connecting portion (not shown) of the inner shaft 614.

The proximal end 674b of the half-cylinder 670b partially overlaps the proximal end 674a of the half-cylinder 670a. The proximal end 674b also is formed with an elongated slot 665 that extends from a location adjacent the post 664b across the portion of the proximal end 674b that overlaps the proximal end 674a. The post 664a of the proximal end 674a of the half-cylinder 670a is received in the slot 665 of the proximal end 674b of the half-cylinder 670b.

A spring 684 is wrapped around both of the posts 664a and 664b. The spring 684 is constructed and is attached to the posts 664a and 664b such that the spring biases the posts away from each other. The bias of the spring 684 thus tends to press the post 664a to the end of the slot 665 farthest from the post 664b. Movement of the posts 664a and 664b relative to each other also produces corresponding movement of the half-cylinders 670a and 670b relative to each other. Each proximal end 674a and 674b is also formed with an inclined surface 666a and 666b. Each of the inclined surfaces 666a and 666b extends from a point adjacent the corresponding post 664a and 664b to the curved outer circumference of the corresponding half-cylinder 670a and 670b. The inclined surface 666b is also disposed on a side of its corresponding post 664b opposite the slot 665.

Each half-cylinder 670a, 670b of the cutting head 628 has an outer surface 642 with a generally semi-circular shape when viewed in a cross-section taken radially or perpendicular to the central longitudinal axis 632 of the inner shaft 614. The outer surface 642 extends for the length of the cutting head 628. The cutting head 628 also has an inner surface 644 that is generally parallel to the outer surface 642. The inner surface 644 of each half-cylinder 670a, 670b of the cutting head 628 is a tissue-receiving surface. Each tissue-receiving surface 644 is, in effect, recessed from the outer surface 642 so as to define a depression for receiving a tissue sample, as described below. Along one longitudinally extending side, each tissue-receiving surface 644, when viewed in cross-section taken radially or perpendicular to the length and the central longitudinal axis 632 of the inner shaft 614, adjoins or intersects a narrow, angled surface 657 extending from a first portion 656 of the outer surface 642. This narrow, angled surface 657 intersects the first portion 656 of the outer surface 642 to define a sharpened cutting edge 658 that extends in a straight line lengthwise of the inner shaft 614. Along the opposite longitudinally extending side, the tissue-receiving surface 644 intersects a narrow, radially extending surface 659 that extends between and joins the tissue-receiving surface 644 and the outer surface 642. The radially extending surface 659 is not sharpened nor are its intersections with the tissue-receiving surface 644 and the outer surface 642 sharpened. Neither the surface 659 nor either of the intersections defines a cutting edge.

The distance along the tissue-receiving surface 644 from its intersection with the narrow, angled surface 657 to the intersection between the tissue-receiving surface 644 and the narrow, radially extending surface 659 is substantially greater than the combined distances across the narrow, angled surface and across the narrow, radially extending surface 659. Consequently, the distance along the tissue-receiving surface constitutes a majority of the total distance between the cutting edge 658 and the intersection between the radially extending surface 659 and the outer surface 642, which intersection is adjacent to a second portion 660 of the outer surface that is spaced apart from the portion 656 adjacent the cutting edge 658. The tissue-receiving surface 644 is a continuous surface free of any opening.

When the outer surface 642 of the inner shaft 614 is viewed in cross-section taken radially of or perpendicular to the central longitudinal axis 632 and the length of the inner shaft, each second portion 660 of the outer surface is (a) disposed circumferentially between the two first portions 656 of the outer surface and (b) separated circumferentially from the other second portion by each of the two first portions. In other words, the second portions 660 of the outer surface 642 are interposed circumferentially between the first portions 656 of the outer surface.

In use, the tissue sampling device 600 is operated and functions in a manner similar to the tissue sampling device 200 of FIGS. 7A-7D. The tissue sampling device 600 is first placed in its closed condition with the outer sheath (not shown) positioned adjacent the distal end 638 of the cutting head 628 and the two half-cylinders 670a, 670b facing each other and aligned with each other, as shown in FIG. 13. The sharpened distal end (not shown) of the outer sheath (not shown) is then pressed against a patient's skin adjacent to or overlying (i.e., lying or extending above and across) a target area of tissue. When the sharpened distal end of the outer sheath pierces the skin, the tissue sampling device 600 is advanced into the patient's tissue until the cutting head 628 of the inner shaft 614 is positioned in the target area. Penetration of the skin can be facilitated by forming the distal ends 672a and 672b of the half-cylinders 670a and 670b with optional pointed and sharpened tips (not shown). The outer sheath (not shown) is then retracted or moved proximally relative to the inner shaft 614. The proximal movement of the outer sheath 612 permits the spring 684 to bias or force the two posts 664a and 664b away from each other. As the two posts 664a and 664b move away from each other, the two half-cylinders 670a, 670b also move laterally or slide away from each other in a radial direction. With the tissue sampling device 600 thus in its open condition, as shown in FIG. 14, the tissue sampling device and the cutting head 628 of the inner shaft 614 are rotated about the length of the inner shaft 614 and about the central longitudinal axis 632 of the inner shaft 614, which is also the central longitudinal axis of the tissue sampling device. Rotation of the tissue sampling device 600 and the cutting head 628 causes the two cutting edges 658 of the cutting head to cut two tissue samples from the adjacent tissue.

As the tissue sampling device 600 and the cutting head 628 of the inner shaft 614 are rotated, the two tissue samples are sheared from the larger mass of tissue and are moved onto the tissue-receiving surfaces 644 of the cutting head. After the tissue sampling device 600 and the cutting head 628 of the inner shaft 614 have been rotated through an arc of 180°, each of the cutting edges 658 reaches the point in the larger mass of tissue from which the other tissue sample has been cut. The outer sheath (not shown) is then moved distally relative to the inner shaft 614 so that the sharpened distal end (not shown) of the outer sheath moves or rides along the inclined surfaces 666a and 666b and thereby forces the two half-cylinders 570a, 570b into a closed position facing each other and aligned with each other. The distal movement of the outer sheath also ensures that the two tissue samples are completely severed from the larger mass of tissue. The two tissue samples, which are separate from each other, are then both completely enclosed within the tissue sampling device 600. The tissue sampling device 600 is removed from the patient, and the two tissue samples can be removed from the tissue sampling device for analysis.

Figures 15, 16:
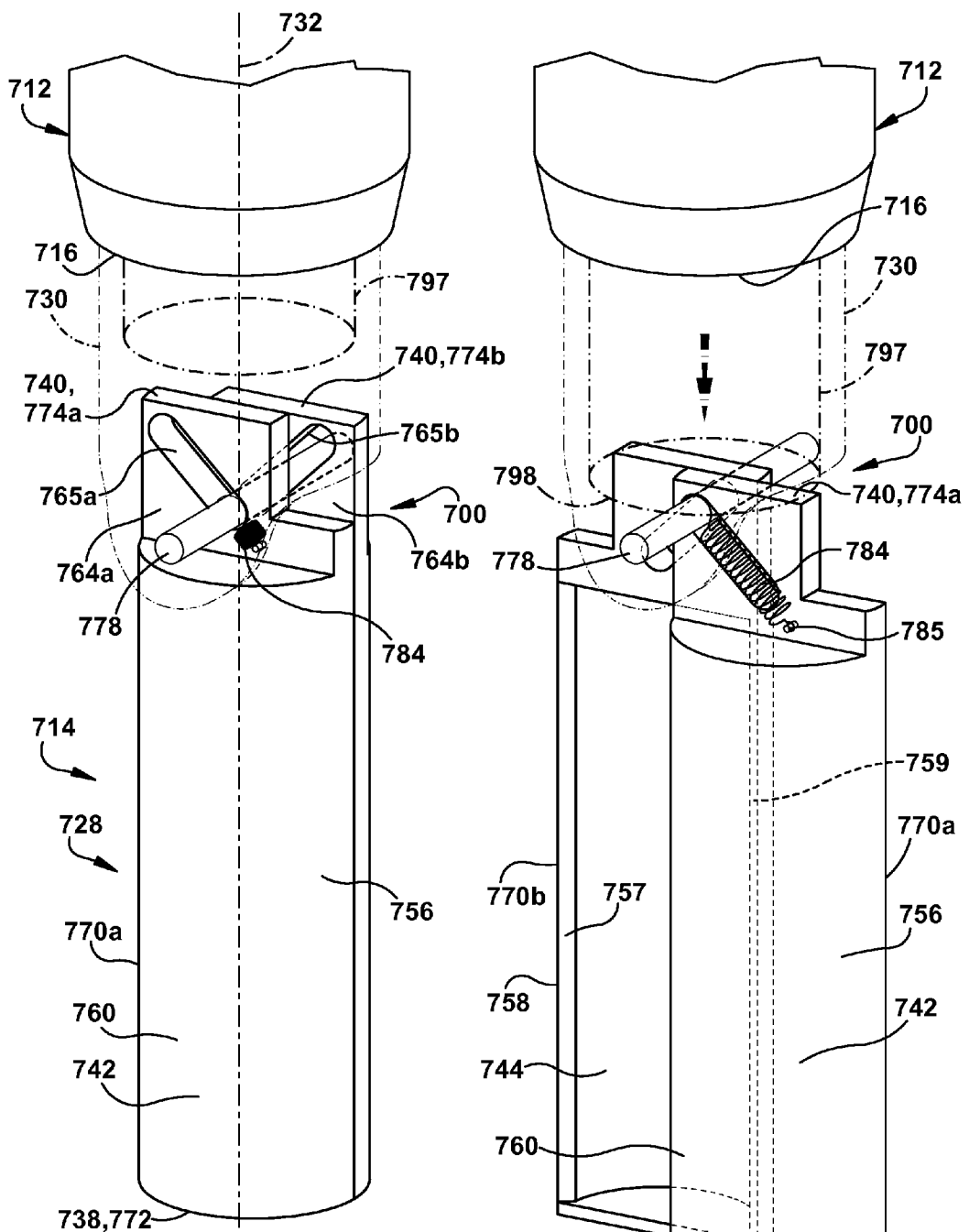
FIG. 15 is a perspective view of a tissue sampling device in accordance with an eighth embodiment of the present invention in a first stage of deployment.
FIG. 16 is a perspective view of the tissue sampling device of FIG. 15 in a second stage of deployment.

FIGS. 15 and 16 illustrate a sixth example mechanism for implementing the operation of the two half-cylinders. The tissue sampling device 700 of FIGS. 15 and 16 incorporates many structural elements that are substantially similar to elements of the tissue sampling device 200 of FIGS. 7A-7D. Similar structural elements are given the same reference numerals as the corresponding structural elements of FIGS. 7A-7D, but increased by 500.

In the tissue sampling device 700 of FIGS. 15 and 16, the pivoting motion of the half-cylinders 270 is replaced with sliding motion. Also, as in the tissue sampling device 400 of FIGS. 10 and 11, a longitudinally movable central post 797 causes the scoops or half-cylinders 770a and 770b to move away from each other so that the cutting edge 758 on each half-cylinder 770a, 770b is exposed to adjacent tissue. Like the half-cylinders 270 of the tissue sampling device of FIGS. 7A-7D, each half-cylinder 770a, 770b of the cutting head 728 of the tissue sampling device 700 has a closed distal end 772 that is coincident with the distal end 738 of the cutting head and a closed proximal end 774a, 774b that is coincident with the proximal end 740 of the cutting head. At its proximal end 774a, 774b, each half-cylinder 770a, 770b is joined to the proximal connecting portion 730 of the inner shaft 714 via an axle 778.

The proximal ends 774a and 774b of the half-cylinders 770a and 770b, respectively, are formed with proximally extending flanges 764a and 764b. The flanges 764a and 764b are positioned along the diametrically-extending edges of the corresponding proximal ends 774a and 774b. The flanges 764a and 764b are formed with elongated slots 765a and 765b that extend diagonally across the flanges from a relatively proximal location adjacent the outer circumference of the corresponding half-cylinder 770a, 770b to a relatively distal location adjacent the mid-point of the proximal end 774a, 774b of the corresponding half-cylinder. The axle 778 is received in both of the elongated slots 765a and 765b. A spring 784 is attached at one end to the axle 778 and is attached at its opposite end to a short post 785 projecting laterally from the flange 764a adjacent the distal end of the slot 765a. The spring 784 is constructed and is attached to the axle 778 and the short post 785 such that the spring biases or pulls the axle toward the distal end of the slot 765a and toward the short post. Movement of the axle 778 relative to the short post 785 and toward the distal end of the slot 765a also produces corresponding movement of both of the half-cylinders 770a and 770b relative to each other.

Each half-cylinder 770a, 770b of the cutting head 728 has an outer surface 742 with a generally semi-circular shape when viewed in a cross-section taken radially or perpendicular to the length and the central longitudinal axis 732 of the inner shaft 714. The outer surface 742 extends for the length of the cutting head 728. The cutting head 728 also has an inner surface 744 that is generally parallel to the outer surface 742. The inner surface 744 of each half-cylinder 770a, 770b of the cutting head 728 is a tissue-receiving surface. Each tissue-receiving surface 744 is, in effect, recessed from the outer surface 742 so as to define a depression for receiving a tissue sample, as described below. Along one longitudinally extending side, each tissue-receiving surface 744, when viewed in cross-section taken radially or perpendicular to the length and the central longitudinal axis 732 of the inner shaft 714, adjoins or intersects a narrow, angled surface 757 extending from a first portion 756 of the outer surface 742. This narrow, angled surface 757 intersects the first portion 756 of the outer surface 742 to define a sharpened cutting edge 758 that extends in a straight line lengthwise of the inner shaft 714. Along the opposite longitudinally extending side, the tissue-receiving surface 744 intersects a narrow, radially extending surface 759 that extends between and joins the tissue-receiving surface 744 and the outer surface 742. The radially extending surface 759 is not sharpened nor are its intersections with the tissue-receiving surface 744 and the outer surface 742 sharpened. Neither the surface 759 nor either of the intersections defines a cutting edge.

The distance along the tissue-receiving surface 744 from its intersection with the narrow, angled surface 757 to the intersection between the tissue-receiving surface 744 and the narrow, radially extending surface 759 is substantially greater than the combined distances across the narrow, angled surface and across the narrow, radially extending surface 759. Consequently, the distance along the tissue-receiving surface constitutes a majority of the total distance between the cutting edge 758 and the intersection between the radially extending surface 759 and the outer surface 742, which intersection is adjacent to a second portion 760 of the outer surface that is spaced circumferentially apart from the first portion 756 adjacent the cutting edge 758. The tissue-receiving surface 744 is a continuous surface free of any opening.

When the outer surface 742 of the inner shaft 714 is viewed in cross-section taken radially of or perpendicular to the central longitudinal axis 732 and the length of the inner shaft, each second portion 760 of the outer surface is (a) disposed circumferentially between the two first portions 756 of the outer surface and (b) separated circumferentially from the other second portion by each of the two first portions. In other words, the second portions 760 of the outer surface 742 are interposed circumferentially between the first portions 756 of the outer surface.

In use, the tissue sampling device 700 is operated and functions in a manner similar to the tissue sampling device 200 of FIGS. 7A-7D. The tissue sampling device 700 is first placed in its closed condition with the outer sheath 712 positioned adjacent the distal end 738 of the cutting head 728 and the two half-cylinders 770a, 770b facing each other and aligned with each other, as shown in FIG. 15, but with the outer sheath shown in a proximal position for clarity. The sharpened distal end 716 of the outer sheath 712 is then pressed against a patient's skin adjacent to or overlying (i.e., lying or extending above and across) a target area of tissue. When the sharpened distal end 716 of the outer sheath pierces the skin, the tissue sampling device 700 is advanced into the patient's tissue until the cutting head 728 of the inner shaft 714 is positioned in the target area. Penetration of the skin can be facilitated by forming the distal ends 772a and 772b of the half-cylinders 770a and 770b with optional pointed and sharpened tips (not shown). The outer sheath 712 is then retracted or moved proximally relative to the inner shaft 714 until the cutting head 728 of the inner shaft is exposed adjacent to tissue of the target area. The central post 797 is moved distally relative to the tubular inner shaft 714 so that a flat bottom surface 798 of the central post presses on the flat proximal surfaces of the flanges 764a and 764b at the proximal ends of the half-cylinders 770a, 770b to bias or force the two half-cylinders to move distally relative to the tubular inner shaft 714.

The distal movement of the half-cylinders 770a and 770b relative to the tubular inner shaft 714 causes the axle 778, which is attached to the inner shaft, to move proximally along the inclined slots 765a and 765b in the flanges 764a and 764b. Movement of the axle 778 proximally along the slots 765a and 765b stretches or elongates the spring 784 and causes the two half-cylinders 770a, 770b also move laterally or slide away from each other in a radial direction into the position shown in FIG. 16. With the tissue sampling device 700 thus in its open condition, the tissue sampling device and the cutting head 728 of the inner shaft 714 are rotated about the length of the inner shaft 714 and about the central longitudinal axis 732 of the inner shaft 714, which is also the central longitudinal axis of the tissue sampling device. Rotation of the tissue sampling device 700 and the cutting head 728 causes the two cutting edges 758 of the cutting head to cut two tissue samples from the adjacent tissue.

As the tissue sampling device 700 and the cutting head 728 of the inner shaft 714 are rotated, the two tissue samples are sheared from the larger mass of tissue and are moved onto the tissue-receiving surfaces 744 of the cutting head. After the tissue sampling device 700 and the cutting head 728 of the inner shaft 714 have been rotated through an arc of 180°, each of the cutting edges 758 reaches the point in the larger mass of tissue from which the other tissue sample has been cut. The central post 797 is then moved proximally relative to the inner shaft 714 so that that the spring 784 can contract and bias or force the two half-cylinders 770a, 770b into a closed position facing each other and aligned with each other. The outer sheath 712 is then moved distally relative to the inner shaft 714 to ensure that the two tissue samples are completely severed from the larger mass of tissue. The two tissue samples, which are separate from each other, are then both completely enclosed within the tissue sampling device 700. The tissue sampling device 700 is removed from the patient, and the two tissue samples can be removed from the tissue sampling device for analysis.

FIGS. 17 through 20 illustrate a seventh example mechanism for implementing the operation of two half-cylinders. The tissue sampling device 800 of FIGS. 17-20 incorporates many structural elements that are substantially similar to elements of the tissue sampling device 200 of FIGS. 7A-7D. Similar structural elements are given the same reference numerals as the corresponding structural elements of FIGS. 7A-7D, but increased by 600.

In the tissue sampling device 800 of FIGS. 17-20, the pivoting motion of the scoops or half-cylinders 270 is replaced with sliding motion. Also, the spring 284 of the tissue sampling device 200 is eliminated. Like the half-cylinders 270 of the tissue sampling device of FIGS. 7A-7D, each half-cylinder 870a, 870b of the cutting head 828 of the tissue sampling device 800 has a closed distal end 872 that is coincident with the distal end 838 of the cutting head and a closed proximal end 874a, 874b that is coincident with the proximal end 840 of the cutting head. At its proximal end 874a, 874b, each half-cylinder 870a, 870b is joined to the proximal connecting portion 830 of the inner shaft 814. The proximal ends 874a and 874b of the half-cylinders 870a and 870b, respectively, are formed with proximally extending posts 864a and 864b. The posts 864a and 864b are positioned approximately mid-way across the diametrically-extending edges of the corresponding proximal ends 874a and 874b. The proximal end 874b of the half-cylinder 870b partially overlaps the proximal end 874a of the half-cylinder 870a. The proximal end 874b also is formed with an elongated slot 865 that extends from a location adjacent the post 864b across the proximal end. The post 864a of the proximal end 874a of the half-cylinder 870a is received in the slot 865 of the proximal end 874b of the half-cylinder 870b.

The post 864b of the proximal end 874b of the half-cylinder 870b is rotatably mounted at its distal end in the proximal end of the half-cylinder. At its proximal end, the post 864b is connected to the proximal connecting portion 830 so that the post 864b and the proximal connecting portion move together and, more specifically, rotate together. The connection between the post 864b and the proximal connecting portion 830 may be achieved by forming both the post and the proximal connecting portion in one piece. The post 864b and the proximal connecting portion 830 are also both connected to a semi-circular guide member 866 for joint rotation with the guide member. The connection to the guide member 866 is adjacent one corner of the guide member, where an arcuate portion of the peripheral edge of the guide member meets a linear portion of the peripheral edge. The guide member 866 has a semi-circular guide slot 867 formed adjacent the arcuate portion of the peripheral edge or outer periphery of the guide member. The post 864a of the half-cylinder 870a is received in the guide slot 867. The post 864a has an enlarged head so that the post and the half-cylinder 870a remain connected to the guide member 866 and the proximal connecting portion 830.

Rotational movement of the proximal connecting portion 830 and the post 864b produces corresponding rotational movement of the guide member 866. Clockwise rotation of the guide member 866, as viewed in FIG. 17, causes movement of the post 864a along the guide slot 867. Movement of the post 864a along the guide slot 867 also results in movement of the post 864a along the slot 865 in a radially outward direction. Movement of the post 864a along the slot 865 produces corresponding movement of the half-cylinders 870a and 870b laterally or radially relative to each other.

Each half-cylinder 870a, 870b of the cutting head 828 has an outer surface 842 with a generally semi-circular shape when viewed in a cross-section taken radially or perpendicular to the central longitudinal axis 832 of the inner shaft 814. The outer surface 842 extends for the length of the cutting head 828. The cutting head 828 also has an inner surface 844 that is generally parallel to the outer surface 842. The inner surface 844 of each half-cylinder 870a, 870b of the cutting head 828 is a tissue-receiving surface. Each tissue receiving surface 844 is, in effect, recessed from the outer surface 842 so as to define a depression for receiving a tissue sample, as described below. Along one longitudinally extending side, each tissue-receiving surface 844, when viewed in cross-section taken radially or perpendicular to the length and the central longitudinal axis 832 of the inner shaft 814, adjoins or intersects a narrow, angled surface 857 extending from a first portion 856 of the outer surface 842. This narrow, angled surface 857 intersects the first portion 856 of the outer surface 842 to define a sharpened cutting edge 858 that extends in a straight line lengthwise of the inner shaft 814. Along the opposite longitudinally extending edge, the tissue-receiving surface 844 intersects a narrow, radially extending surface 859 that extends between and joins the tissue-receiving surface 844 and the outer surface 842. The radially extending surface 859 is not sharpened nor are its intersections with the tissue-receiving surface 844 and the outer surface 842 sharpened. Neither the surface 859 nor either of the intersections defines a cutting edge.

The distance along the tissue-receiving surface 844 from its intersection with the narrow, angled surface 857 to the intersection between the tissue-receiving surface 844 and the narrow, radially extending surface 859 is substantially greater than the combined distances across the narrow, angled surface and across the narrow, radially extending surface 859. Consequently, the distance along the tissue-receiving surface constitutes a majority of the total distance between the cutting edge 858 and the intersection between the radially extending surface 859 and the outer surface 842, which intersection is adjacent to a second portion 860 of the outer surface that is spaced circumferentially apart from the first portion 856 adjacent the cutting edge 858. The tissue-receiving surface 844 is a continuous surface free of any opening.

When the outer surface 842 of the inner shaft 814 is viewed in cross-section taken radially of or perpendicular to the central longitudinal axis 832 and the length of the inner shaft, each second portion 860 of the outer surface is (a) disposed circumferentially between the two first portions 856 of the outer surface and (b) separated circumferentially from the other second portion by each of the two first portions. In other words, the second portions 860 of the outer surface 842 are interposed circumferentially between the first portions 856 of the outer surface.

In use, the tissue sampling device 800 is operated and functions in a manner similar to the tissue sampling device 200 of FIGS. 7A-7D. The tissue sampling device 800 is first placed in its closed condition with the outer sheath (not shown) positioned adjacent the distal end 838 of the cutting head 828 and the two half-cylinders 870a, 870b facing each other and aligned with each other, as shown in FIGS. 17 and 19. The sharpened distal end (not shown) of the outer sheath (not shown) is then pressed against a patient's skin adjacent to or overlying (i.e., lying or extending above and across) a target area of tissue. When the sharpened distal end (not shown) of the outer sheath pierces the skin, the tissue sampling device 800 is advanced into the patient's tissue until the cutting head 828 of the inner shaft 814 is positioned in the target area. Penetration of the skin can be facilitated by forming the distal ends 872a and 872b of the half-cylinders 870a and 870b with optional pointed and sharpened tips (not shown). The outer sheath (not shown) is then retracted or moved proximally relative to the inner shaft 814 until the cutting head 828 of the inner shaft is exposed adjacent to tissue of the target area.

The proximal connecting portion 830 is rotated in a clockwise direction, as viewed in FIG. 17, about its central axis to rotate the post 864b and the guide member 866. Clockwise rotation of the proximal connecting portion 830, the post 864b, and the guide member 866 causes movement of the post 864a along the guide slot 867. Movement of the post 864a along the guide slot 867 also results in movement of the post 864a along the slot 865 in a radially outward direction. Movement of the post 864a along the guide slot 867 causes the half-cylinders 870a and 870b to move laterally or slide away from each other in a radial direction into the position shown in FIGS. 18 and 20. With the tissue sampling device 800 thus in its open condition, the tissue sampling device and the cutting head 828 of the inner shaft 814 are rotated about the length of the inner shaft 814 and about the central longitudinal axis 832 of the inner shaft 814, which is also the central longitudinal axis of the tissue sampling device. Rotation of the tissue sampling device 800 and the cutting head 828 causes the two cutting edges 858 of the cutting head to cut two tissue samples from the adjacent tissue.

As the tissue sampling device 800 and the cutting head 828 of the inner shaft 814 are rotated, the two tissue samples are sheared from the larger mass of tissue and are moved onto the tissue-receiving surfaces 844 of the cutting head. After the tissue sampling device 800 and the cutting head 828 of the inner shaft 814 have been rotated through an arc of 180°, each of the cutting edges 858 reaches the point in the larger mass of tissue from which the other tissue sample has been cut. The proximal connecting portion 830 is then rotated in a counter-clockwise direction to move the post 864a along the guide slot 867 and radially inwardly along the slot 865. This motion of the post 864a moves the two half-cylinders 870a, 870b into a closed position facing each other and aligned with each other. The outer sheath (not shown) is then moved distally relative to the inner shaft 814 to ensure that the two tissue samples are completely severed from the larger mass of tissue. The two tissue samples, which are separate from each other, are then both completely enclosed within the tissue sampling device 800. The tissue sampling device 800 is removed from the patient, and the two tissue samples can be removed from the tissue sampling device for analysis.

FIGS. 21 through 24 illustrate an eighth example mechanism for implementing the operation of two half-cylinders. The tissue sampling device 900 of FIGS. 21-24 incorporates many structural elements that are substantially similar to elements of the tissue sampling device 200 of FIGS. 7A-7D. Similar structural elements are given the same reference numerals as the corresponding structural elements of FIGS. 7A-7D, but increased by 700.

In the tissue sampling device 900 of FIGS. 21-24, the pivoting motion of the half-cylinders 270 is replaced with sliding motion. Also, the spring 284 of the tissue sampling device 200 is eliminated. Like the half-cylinders 270 of the tissue sampling device of FIGS. 7A-7D, each scoop or half-cylinder 970a, 970b of the cutting head 928 of the tissue sampling device 900 has a closed distal end (not shown) that is coincident with the distal end (not shown) of the cutting head and a closed proximal end 974a, 974b that is coincident with the proximal end 940 of the cutting head. At its proximal end 974a, 974b, each half-cylinder 970a, 970b is joined to the proximal connecting portion 930 of the inner shaft 914. The proximal ends 974a and 974b of the half-cylinders 970a and 970b, respectively, are formed with proximally extending posts 964a and 964b. The posts 964a and 964b are positioned approximately mid-way across the diametrically-extending edges of the corresponding proximal ends 974a and 974b. A circular guide member 966 is mounted adjacent to, but proximally of the two half-cylinders 970a and 970b. The circular guide member 966 is mounted to the tubular proximal connecting portion 930 so as to be held against rotational movement. Two arcuate guide slots 967a and 967b are formed in the circular guide member 966. Each of the guide slots 967a and 967b curves from a point adjacent the outer circumference of the guide member 966 to a point near, but spaced radially from the center of the guide member. Each of the guide slots 967a and 967b receives a corresponding one of the two posts 964a and 964b, respectively, so that the posts move along the guide slots. The posts 964a and 964b have enlarged heads so that the posts and the half-cylinders 970a and 970b remain connected to the guide member 966 and the proximal connecting portion 930

A diametrically extending vane 968 is mounted adjacent to, but proximally of the guide member 966. The vane 968 is attached at its center to a rotatable shaft 969, which extends longitudinally within the tubular proximal connecting portion 930 of the inner shaft 914. Rotation of the shaft 969 causes rotation of the vane 968. Rotation of the vane 968, in turn, causes the vane to push on the posts 964a and 964b attached to the half-cylinders 970a and 970b, respectively. Because movement of the posts 964a and 964b is constrained by the guide slots 967a and 967b in the non-rotating guide member 966, the resulting movement of the posts is movement along the arcuate guide slots. Movement of the posts 964a and 964b along the guide slots 967a and 967b produces corresponding movement of the half-cylinders 970a and 970b relative to each other laterally or away from each other in a radial direction.

Figure 21:
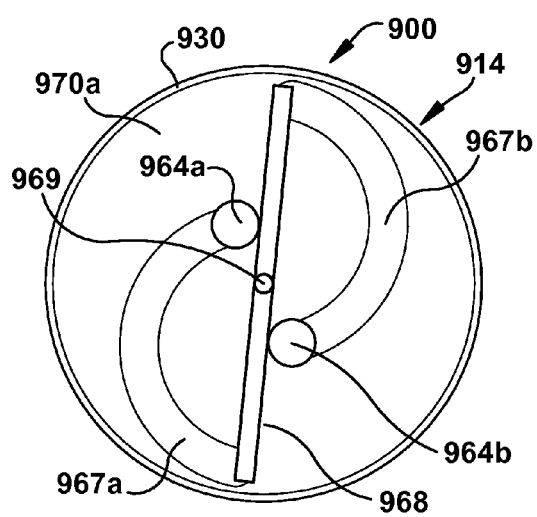
FIG. 21 is a top view of a tissue sampling device in accordance with an eleventh embodiment of the present invention in a first stage of deployment.
Figure 22:
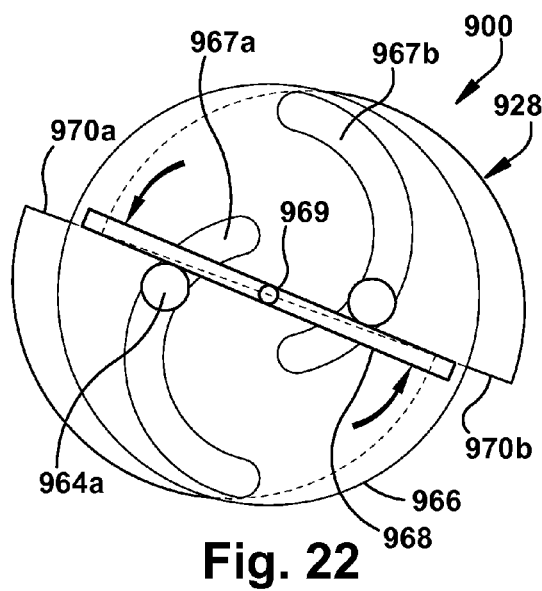
FIG. 22 is a top view of the tissue sampling device of FIG. 21 in a second stage of deployment.
Figure 23:
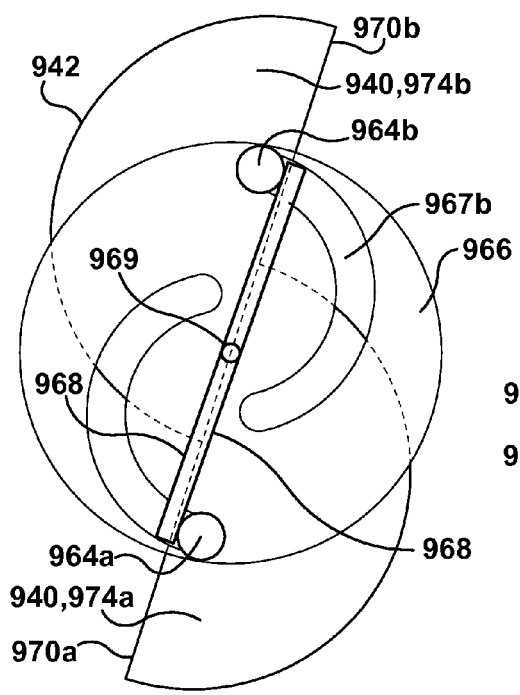
FIG. 23 is a top view of the tissue sampling device of FIG. 21 in a third stage of deployment.

More specifically, as shown in FIG. 21, the cutting head 928 has a closed condition in which the two half-cylinders 870a, 870b face each other and are aligned with each other. When the cutting head 928 is in its closed condition, the posts 964a and 964b at the proximal ends 974a and 974b of the half-cylinders 970a and 970b are at the radially innermost ends of the guide slots 967a and 967b in the guide member 966. If the shaft 969 and the vane 968 are rotated in a counter-clockwise direction until the vane contacts the posts 964a and 964b, the vane and the posts will be in the position shown in FIG. 21. Continued counter-clockwise rotation of the vane 968 will push the posts 964a and 964b radially outward along the guide slots 967a and 967b in the non-rotating guide member 966. FIG. 22 shows the vane 968 and the posts 964a and 964b in an intermediate position during such counter-clockwise rotation of the vane. As can be seen, the half-cylinders 970a and 970b are simultaneously being pushed laterally or radially outward and away from each other. When the posts 964a and 964b reach the radially outermost ends of the guide slots 967a and 967b, as shown in FIG. 23, the half-cylinders 970a and 970b have been moved to their greatest radial displacement relative to each other, and the cutting head 928 is in its fully open condition.

Figure 24:
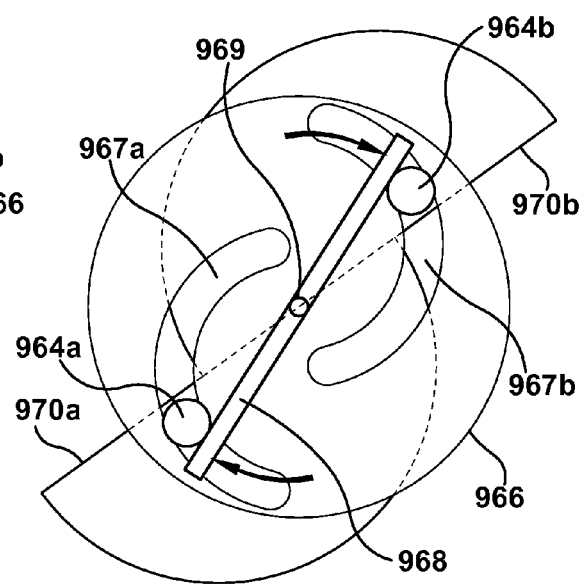
FIG. 24 is a top view of the tissue sampling device of FIG. 21 in a fourth stage of deployment.

To return the cutting head 928 and the half-cylinders 970a and 970b to a closed condition, the shaft 969 and the vane 968 are rotated in a clockwise direction. Initially, the vane 968 moves away from the adjacent posts 964a and 964b, but the vane ultimately again contacts the posts after rotating through an arc of slightly less than 180°. With the vane 968 again in contact with the posts 964a and 964b, continued clockwise rotation of the vane pushes the posts back along their respective guide slots 967a and 967b in the guide member 966 toward the radially inner most ends of the guide slots. FIG. 24 shows the vane 968 and the posts 964a and 964b in an intermediate position during such clockwise rotation of the vane. When the posts 964a and 964b reach the radially innermost ends of the guide slots 967a and 967b, the half-cylinders 970a and 970b have again been moved to face each other and to be aligned with each other, and the cutting head 928 is in its fully closed condition.

Each half-cylinder 970a, 970b of the cutting head 928 has an outer surface 942 with a generally semi-circular shape when viewed in a cross-section taken radially or perpendicular to the length and the central longitudinal axis (not shown) of the inner shaft 914. The outer surface 942 extends for the length of the cutting head 928. The cutting head 928 also has an inner surface (not shown) that is generally parallel to the outer surface 942. The inner surface (not shown) of each half-cylinder 970*a*, 970*b* of the cutting head 928 is a tissue-receiving surface. Each tissue-receiving surface (not shown) is, in effect, recessed from the outer surface 942 so as to define a depression for receiving a tissue sample, as described below. Except for their proximal ends 974*a* and 974*b*, the half-cylinders 970*a* and 970*b* are in all respects identical to the half-cylinders 870*a* and 870*b* of FIGS. 17-20.

In use, the tissue sampling device 900 is operated and functions in a manner similar to the tissue sampling device 800 of FIGS. 17-20. The tissue sampling device 900 is first placed in its closed condition with the outer sheath (not shown) positioned adjacent the distal end (not shown) of the cutting head 928 and with the two half-cylinders 970*a*, 970*b* facing each other and aligned with each other, as shown in FIG. 21. The sharpened distal end (not shown) of the outer sheath (not shown) is then pressed against a patient's skin adjacent to or overlying (i.e., lying or extending above and across) a target area of tissue. When the sharpened distal end (not shown) of the outer sheath pierces the skin, the tissue sampling device 900 is advanced into the patient's tissue until the cutting head 928 of the inner shaft 914 is positioned in the target area. Penetration of the skin can be facilitated by forming the distal ends 972*a* and 972*b* of the half-cylinders 970*a* and 970*b* with optional pointed and sharpened tips (not shown). The outer sheath (not shown) is then retracted or moved proximally relative to the inner shaft 914 until the cutting head 928 of the inner shaft is exposed adjacent to tissue of the target area.

The vane 968 is rotated in a counter-clockwise direction, as viewed in FIG. 21, about its central axis (not shown) and about the shaft 969 to push the posts 964*a* and 964*b* in the guide slots 967*a* and 967*b* of the guide member 966. Movement of the posts 964*a* and 964*b* along the guide slots 967*a* and 967*b* causes the half-cylinders 970*a* and 970*b* to move laterally or slide away from each other in a radial direction into the position shown in FIG. 23. With the tissue sampling device 900 thus in its open condition, the tissue sampling device and the cutting head 928 of the inner shaft 914 are rotated about the length of the inner shaft 914 and about the central longitudinal axis (not shown) of the inner shaft 914, which is also the central longitudinal axis of the tissue sampling device. Rotation of the tissue sampling device 900 and the cutting head 928 causes the two cutting edges (not shown) of the cutting head to cut two tissue samples from the adjacent tissue.

As the tissue sampling device 900 and the cutting head 928 of the inner shaft 914 are rotated, the two tissue samples are sheared from the larger mass of tissue and are moved onto the tissue-receiving surfaces (not shown) of the cutting head. After the tissue sampling device 900 and the cutting head 928 of the inner shaft 914 have been rotated through an arc of 180°, each of the cutting edges reaches the point in the larger mass of tissue from which the other tissue sample has been cut. The vane 968 is then rotated in a clockwise direction to move the posts 964*a* and 964*b* back along and radially inwardly in the guide slots 967*a* and 967*b*. This motion of the posts 964*a* and 964*b* moves the two half-cylinders 970*a*, 970*b* into a closed position facing each other and aligned with each other. The outer sheath (not shown) is then moved distally relative to the inner shaft 914 to ensure that the two tissue samples are completely severed from the larger mass of tissue. The two tissue samples, which are separate from each other, are then both completely enclosed within the tissue sampling device 900. The tissue sampling device 900 is removed from the patient, and the two tissue samples can be removed from the tissue sampling device for analysis.

Figure 25:
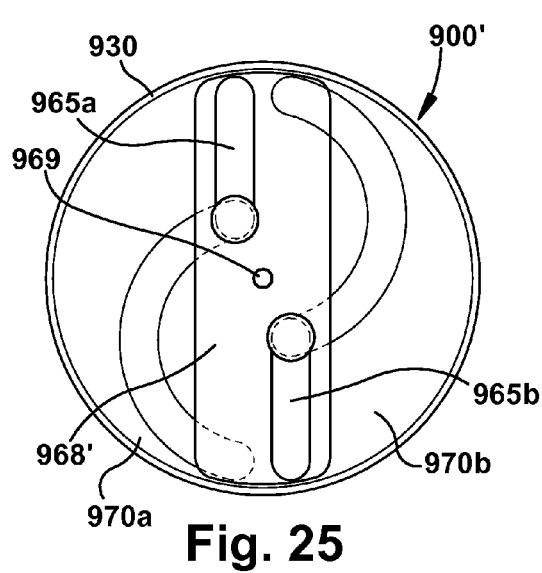
FIG. 25 is a top view of a tissue sampling device in accordance with a modified version of the tissue sampling device of FIGS. 21-24 a first stage of deployment.
Figure 26:
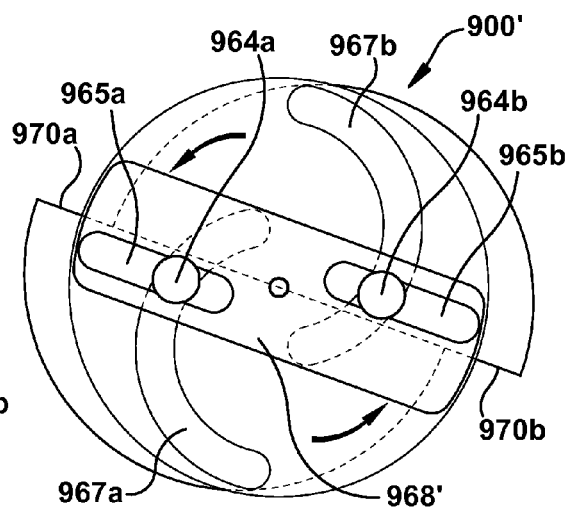
FIG. 26 is a top view of the tissue sampling device of FIG. 25 in a second stage of deployment.

FIGS. 25 and 26 illustrate a modified version of the tissue sampling device 900 of FIGS. 21-24. In the tissue sampling device 900' of FIGS. 25-26, the diametrically extending vane 968 is replaced with a diametrically extending plate 968'. The plate 968' is formed with two slots 965*a* and 965*b*. Each slot 965*a* and 965*b* extends in a straight line from a point adjacent the outer circumference of the plate 968' to a point near, but spaced radially from the center of the plate. Each of the slots 965*a* and 965*b* receives a corresponding one of the two posts 964*a* and 964*b*, respectively, so that the posts move along the guide slots. Rotation of the shaft 969 causes rotation of the plate 968'. Rotation of the plate 968', in turn, causes the posts 964*a* and 964*b* attached to the half-cylinders 970*a* and 970*b*, respectively, to move along the slots 965*a* and 965*b*. At the same time, the posts 964*a* and 964*b* are caused to move along the arcuate guide slots 967*a* and 967*b* in the guide member 966. Because movement of the posts 964*a* and 964*b* is constrained by the arcuate guide slots 967*a* and 967*b* in the non-rotating guide member 966, the resulting movement of the posts is movement along the arcuate guide slots. Radially outward movement of the posts 964*a* and 964*b* along the slots 965*a* and 965*b* is accompanied by radially outward movement of the posts along the arcuate guide slots 967*a* and 967*b*. Similarly, radially inward movement of the posts 964*a* and 964*b* along the slots 965*a* and 965*b* is accompanied by radially inward movement of the posts along the arcuate guide slots 967*a* and 967*b*. Movement of the posts 964*a* and 964*b* along the guide slots 967*a* and 967*b* produces corresponding movement of the half-cylinders 970*a* and 970*b* relative to each other laterally or sliding away from each other in a radial direction, just as in the embodiment of the tissue sampling device 900 shown in FIGS. 21-24.

Figure 27:
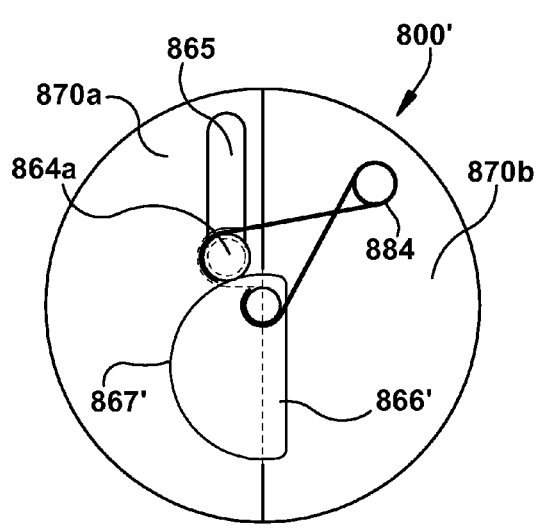
FIG. 27 is a top view of a tissue sampling device in accordance with a modified version of the tissue sampling device of FIGS. 17-20 a first stage of deployment.
Figure 28:
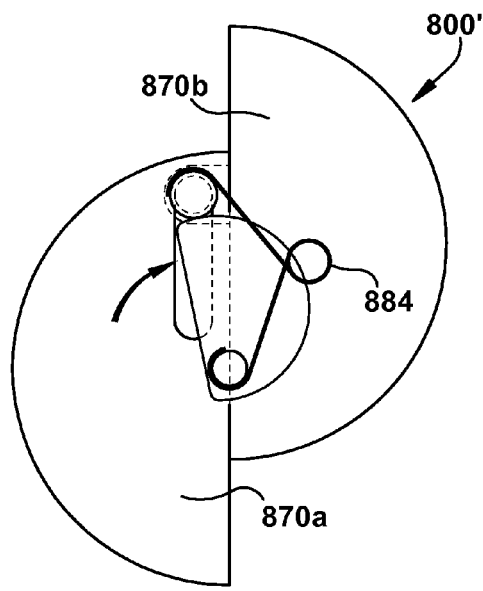
FIG. 28 is a top view of the tissue sampling device of FIG. 27 in a second stage of deployment.

FIGS. 27 and 28 illustrate a modified version of the tissue sampling device 800 of FIGS. 17-20. In the tissue sampling device 800' of FIGS. 27-28, the semi-circular guide member 866 is replaced with a cam 866'. The cam 866' is formed with an outer circumference 867' shaped like a portion of a logarithmic spiral. The post 864*b* and the proximal connecting portion 830 are connected to the cam 866' at a point closest to the center of the portion of the spiral. Rotational movement of the proximal connecting portion 830 and the post 864*b* produces corresponding rotational movement of the cam 866'. Clockwise rotation of the guide member 866, as viewed in FIG. 27, causes movement of the post 864*a* along the slot 865 in a radially outward direction. Movement of the post 864*a* along the slot 865 produces corresponding movement of the half-cylinders 870*a* and 870*b* relative to each other. Because radially outward movement of the post 864*a* is produced by movement of the post along the outer circumference 867' of the cam 866', rather than movement in a slot, radially inward movement of the post 864*a* is accomplished using the bias of a spring 884 mounted between the posts 864*a* and 864*b*. The spring 884 urges the posts 864*a* and 864*b* toward each other. Radially inward movement of the post 864*a* is accompanied by counter-clockwise rotation of the post 864*b* and the proximal connecting portion 830 to move the cam 866' so that a relatively small portion of the cam is interposed between the posts 864*a* and 864*b*.

With each of the foregoing embodiments of a tissue sampling device in accordance with the present invention, there may be a need for a larger volume of tissue than can be obtained from a single insertion of the device into a patient's body. The larger volume may be necessary or desirable, for example, to ensure greater accuracy of a pathologic diagnosis of the tissue sample. A larger volume of tissue can be obtained by multiple insertions of the tissue sampling device or by using a tissue sampling device with a large diameter or outer circumference. Both such approaches have disadvantages, in terms of either additional discomfort for the patient and/or increased risk of damage to healthy tissue adjacent the targeted biopsy site. Another approach is to apply a vacuum to the tissue sampling device in order to remove each tissue sample as it is cut from the targeted biopsy site. Use of a vacuum removal system potentially allows the tissue sampling device to be inserted only once and then advanced or retracted slightly to obtain multiple tissue samples.

With respect to the present invention, a vacuum removal system for tissue samples can be applied to those embodiments of the invention in which an open passage is provided from the cutting head of the inner shaft through the proximal connecting portion of the inner shaft. The tissue sampling devices 10 and 100 of FIGS. 1-4 and 5-6, respectively, are best suited for use with a vacuum removal system for tissue samples, provided the proximal connecting portions 30 and 130 are formed as hollow or tubular members. A vacuum removal system does, however, require a relatively large and powerful device to create a vacuum sufficiently strong that a tissue sample can be drawn or pulled back through the length of an open passage within the tissue sampling device extending from the portion of the tissue sampling device at which the tissue samples are cut from the patient's body to a location outside the patient's body at which the tissue samples can be removed.

Figure 29:
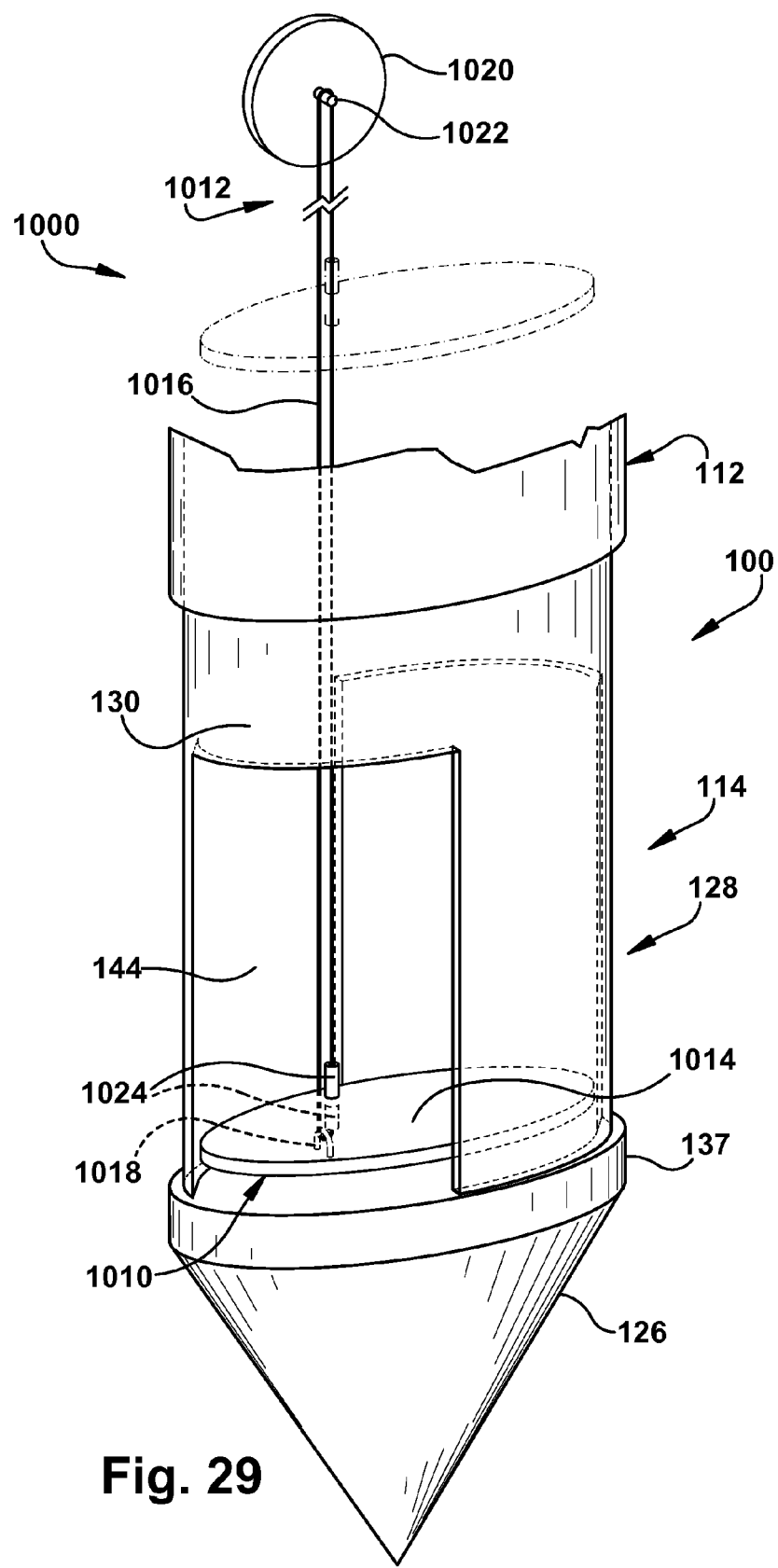
FIG. 29 is a perspective view of the tissue sampling device of FIG. 5 equipped with a tissue sample transport system.

Another approach to removing a tissue sample from a tissue sampling device without removing the tissue sampling device from a patient's body is to use a mechanism to push, rather than pull, the tissue sample from the tissue sampling device. FIG. 29 shows an embodiment of such a tissue pushing mechanism installed in the tissue sampling device 100 illustrated in FIGS. 5 and 6. The mechanical assist device 1000 for removing a tissue sample (not shown) from the tissue sampling device 100 includes a tissue sample platform 1010 and a drive mechanism 1012 to move the tissue sample platform.

The tissue sample platform 1010 is a flat plate 1014 fabricated from a relatively rigid and light weight material, such as a plastic polymer. The flat plate 1014 has an elliptical outer circumference dimensioned to fit within the elliptically shaped inner surface 144 of the cutting heading 128. When positioned to receive a tissue sample, the flat plate 1014 lies on the top surface of the elliptic cylinder portion 137 of the distal tip 126. (The flat plate 1014 is shown in FIG. 29 in a position slightly above the top surface of the elliptic cylinder portion 137 for clarity of illustration.) The flat plate 1014 is thus disposed distally of the tissue sample (not shown) as the tissue sample is cut from the target area of a patient's body.

The drive mechanism 1012 moves the flat plate 1014 in a proximal direction to remove the tissue sample from the tissue sampling device 100. Because the flat plate 1014 is initially located distally of the tissue sample (not shown), the flat plate effectively pushes the tissue sample in a proximal direction out of the cutting head 128 and through the tubular proximal connecting portion 130 of the inner shaft 114 of the tissue sampling device 100. As shown, the drive mechanism 1012 includes a drive loop 1016, an end fitting 1018, and a hand wheel 1020.

The drive loop 1016 of the drive mechanism 1012 is a long strand of material, such as a metal wire or a polymer filament. The material of which the drive loop 1016 is formed should be flexible, yet strong enough to deliver sufficient force to move a tissue sample (not shown) proximally through the tissue sampling device 100. The drive loop 1016 extends lengthwise through the tissue sampling device 100 from a location on or adjacent the elliptic cylinder portion 137 of the distal tip 126 to a location adjacent the proximal end of the tissue sampling device.

At its most distal location, the drive loop 1016 passes through or around the end fitting 1018, which is fixed on or adjacent the elliptic cylinder portion 137 of the distal tip 126. As shown in FIG. 29, the end fitting 1018 is a U-shaped bracket, but the end fitting may have any configuration or structure that will permit the drive loop 1016 to pass through or around the end fitting. At its most proximal location, the drive loop 1016 passes around an axle 1022 secured to the hand wheel 1020 for rotation with the hand wheel. The axle 1022 has an outer surface that is roughened, made tacky or sticky, or otherwise formed to engage the drive loop 1016 and impart a motive force to the drive loop. Intermediate its most distal and proximal locations, the drive loop 1016 is attached to the flat plate 1014 of the tissue sample platform 1010. As shown in FIG. 29, two ferrules 1024 are crimped onto the drive loop 1016 to attach the drive loop to the flat plate 1014. One ferrule 1024 is crimped onto the drive loop 1016 proximally of the flat plate 1014. The other ferrule 1024 is crimped onto the drive loop 1016 distally of the flat plate 1014. The flat plate 1014 is thus held in position on the drive loop 1016 between the two ferrules 1024.

In use, the mechanical assist device 1000 is initially operated to move the tissue sample platform 1010 to its most distal position with the flat plate 1014 in contact with the top surface of the elliptic cylinder portion 137 of the distal tip 126 of the tissue sampling device 100. After tissue samples (not shown) are cut by the cutting head 128 of the tissue sampling device 100, the hand wheel 1020 of the drive mechanism 1012, which is attached to the proximal end of the tissue sampling device, is rotated in a clockwise or counter-clockwise direction to impart a motive force to the drive loop 1016 and to move the tissue sample platform 1010 in a proximal direction. When the tissue sample platform 1010 reaches an appropriate proximal location outside of the patient's body, the tissue samples (not shown) can be removed from the tissue sample platform. The hand wheel 1020 is then rotated in the opposite direction, to return the tissue sample platform 1010 to its most distal position. The tissue sampling device 100 is moved (e.g., advanced or retracted) slightly to position the cutting head 128 adjacent another target area. The foregoing procedure is then repeated as required to obtain a desired or required amount of tissue.

As the tissue sampling device 100 may be manufactured with the expectation that the tissue sampling device will be used with a single patient and then discarded, it may be important to keep the structure of mechanical assist device 1000 as simple as possible in order to minimize the cost of the mechanical assist device. For example, to keep the end fitting 1018 as a U-shaped bracket and to keep the axle 1022 as a short cylinder attached to the hand wheel 1020, it may be desirable to form the drive loop 1016 from two different materials. Specifically, the portion of the drive loop 1016 extending from the proximal ferrule 1024 to and around the axle 1022, when the flat plate 1014 is at its most distal position, may formed from a plastic polymer with a tacky or sticky exterior surface or from a metal wire or polymer filament treated with a tacky or sticky coating. The portion of the drive loop 1016 extending from the distal ferrule 1024 toward the axle 1022, when the flat plate 1014 is at its most distal position, may formed from a plastic polymer with a smooth exterior surface or from a metal wire or polymer filament treated with a low friction coating. Because the tissue sampling device 100 is manufactured to be used with a single patient and then discarded, the drive mechanism 1012 is only required to function properly for a limited number of times.

If it is desired that the mechanical assist device 1000 be operable for a larger number of uses, the drive loop 1016 may be formed as "beaded" chain of plastic or metal. This structure would provide a series of spaced apart beads or other enlargements on the outer surface of the drive loop 1016. The axle 1022 would then have a toothed outer surface to engage the enlarged beads on the drive loop 1016. Particularly, if the drive loop 1016 is formed as a plastic "beaded" chain, the portion of the drive loop that passes around the end fitting 1018 can have a smooth outer surface, rather than a beaded outer surface, thereby allowing the use of a simple end fitting.

Although the mechanical assist device 1000 may be positioned at any convenient location around the circumference of the tissue sampling device 100, one desirable location may be adjacent the narrow, radially extending surface 159 of the cutting head 128. With such a location, the mechanical assist device 1000 is less likely to impede the operation of the cutting head 128.

Figure 30:
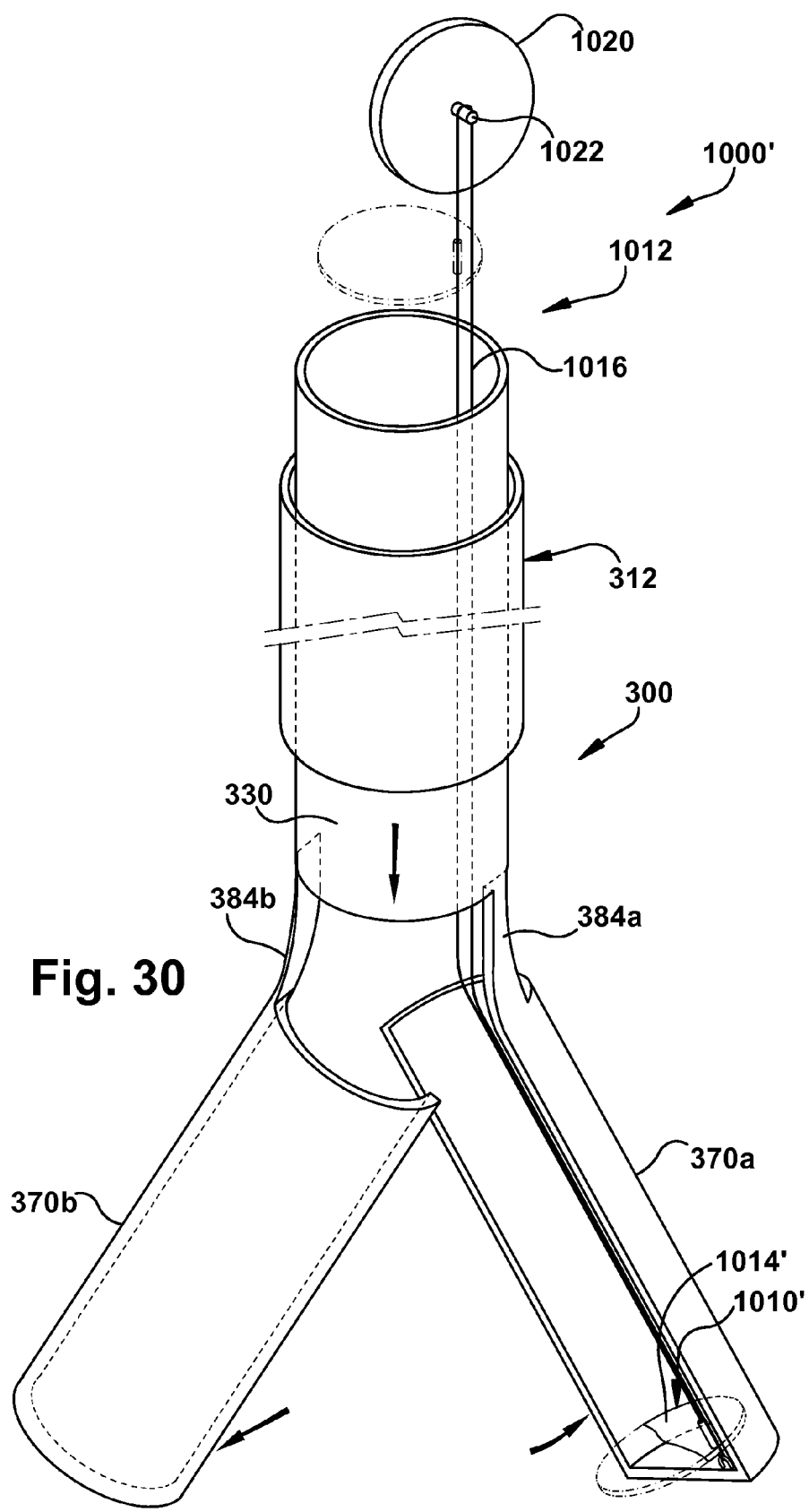
FIG. 30 is a perspective view of the tissue sampling device of FIG. 9 equipped with a tissue sample transport system.

An alternative embodiment of the mechanical assist device 1000 is illustrated in FIG. 30, which shows such an alternative embodiment 1000' installed in the tissue sampling device 300 illustrated in FIGS. 8 and 9. The mechanical assist device 1000' has the same components, structure, and method of operation as the mechanical assist device 1000, except that the flat plate 1014' of the tissue sample platform 1010' has a different shape than the flat plate 1014 of the tissue sample platform 1010. Specifically, the flat plate 1014' has a semi-circular or, possibly circular, outer circumference, rather than an elliptical outer circumference. It may also be necessary to provide two mechanical assist devices 1000' for use with tissue sampling device 300, one mechanical assist device for each half-cylinder 370a and 370b.

In the foregoing descriptions of the tissue sampling devices 200, 300, 400, 500, 600, 700, 800, and 900, the diametrically extending edges of the closed distal ends 238, 338, 438, 538, 638, 738, 838, and 938 of the half-cylinders 270, 370, 470, 570, 670, 770, 870, and 970, respectively, are not described as being sharpened cutting edges. These diametrically extending edges may, however, be sharpened cutting edges in order to facilitate the cutting of tissue samples. Similarly, other edges of the half-cylinders 270, 370, 470, 570, 670, 770, 870, and 970 may be sharpened cutting edges to facilitate the cutting of tissue samples.

From the above description of the invention, those skilled in the art will perceive improvements, changes and modifications. Such improvements, changes, and/or modifications within the skill of the art are intended to be covered by the appended claims.

Having described the invention, the following is claimed:

1. A tissue sampling device for removing tissue from a target area in a body comprising:
    a shaft having a proximal end, a distal end, and a central longitudinal axis extending from the proximal end to the distal end, the shaft also having a length extending in a direction along the longitudinal axis, an outer surface of the shaft extending lengthwise of the shaft, the outer surface including two first portions extending lengthwise of the shaft and two second portions extending lengthwise of the shaft, each first portion of the outer surface being associated with a different second portion and being spaced apart from its associated second portion by a predetermined distance, each first portion of the outer surface at least partially defining a cutting edge extending in a straight line lengthwise of the shaft,
    the shaft further including two tissue-receiving surfaces extending lengthwise of the shaft, each first portion of the outer surface and its associated second portion being associated with a different tissue-receiving surface, each tissue-receiving surface defining a depression for receiving a sample of tissue removed from the target area by the cutting edge defined by its associated first portion of the outer surface when the shaft is rotated about its longitudinal axis in the target area, each tissue-receiving surface extending from adjacent its associated first portion of the outer surface toward its associated second portion of the outer surface for a majority of the predetermined distance between its associated first portion and its associated second portion and providing a continuous surface free of any opening,
    wherein the outer surface of the shaft has an elliptical shape when viewed in cross section taken perpendicular to the longitudinal axis, the elliptical shape having a major axis and a minor axis, each cutting edge being located at the outer surface adjacent the major axis of the elliptical shape.

2. The tissue sampling device of claim 1 further comprising a cannula having a proximal end, a distal end, and an inner surface extending between the proximal end of the cannula and the distal end of the cannula and defining a passage, the inner surface having an elliptical shape when viewed in cross section taken perpendicular to the longitudinal axis, the cannula receiving the shaft with the inner surface of the cannula closely fitting the outer surface of the shaft.

3. The tissue sampling device of claim 1 wherein the outer surface of the shaft when viewed in cross section taken perpendicular to the longitudinal axis has each second portion (a) disposed circumferentially between the two first portions and (b) separated circumferentially from the other second portion by one of the two first portions.

4. The tissue sampling device of claim 1 wherein each tissue-receiving surface and each cutting edge is movable relative to a portion of the shaft adjacent the proximal end of the shaft.

5. The tissue sampling device of claim 4 wherein the two tissue-receiving surfaces are (a) presented toward each other and (b) movable relative to each other.

6. The tissue sampling device of claim 5 wherein the two tissue-receiving surfaces are movable in translation relative to each other.

7. The tissue sampling device of claim 6 further comprising an elongated structure for causing the two tissue-receiving surfaces to move in translation relative to each other.

8. The tissue sampling device of claim 7 wherein the elongated structure is a cannula that receives the shaft.

9. The tissue sampling device of claim 7 wherein the elongated structure is a rod received in a passage formed in and extending along the length of the shaft.

10. The tissue sampling device of claim 5 wherein the two tissue-receiving surfaces are movable pivotally relative to each other.

11. The tissue sampling device of claim 10 further comprising an elongated structure for causing the two tissue-receiving surfaces to move pivotally relative to each other.

12. The tissue sampling device of claim 11 wherein the elongated structure is a cannula that receives the shaft.

13. The tissue sampling device of claim 11 wherein the elongated structure is a rod received in a passage formed in and extending along the length of the shaft.

14. A tissue sampling device for removing tissue from a target area in a body comprising: a shaft having a proximal end, a distal end, and a central longitudinal axis extending from the proximal end to the distal end, the shaft also having a length extending in a direction along the longitudinal axis, an outer surface of the shaft extending lengthwise of the shaft, the outer surface including two first portions extending lengthwise of the shaft and two second portions extending lengthwise of the shaft, each first portion of the outer surface being associated with a different second portion and being spaced apart from its associated second portion by a predetermined distance, each first portion of the outer surface at least partially defining a cutting edge extending lengthwise of the shaft, the shaft further including two tissue-receiving surfaces extending lengthwise of the shaft, each first portion of the outer surface and its associated second portion being associated with a different tissue-receiving surface, each tissue-receiving surface defining a depression for receiving a sample of tissue removed from the target area by the cutting edge defined by its associated first portion of the outer surface when the shaft is rotated about its longitudinal axis in the target area, each tissue-receiving surface extending from adjacent its associated first portion of the outer surface toward its associated second portion of the outer surface for a majority of the predetermined distance between its associated first portion and its associated second portion and providing a continuous surface free of any opening, the outer surface of the shaft having an elliptical shape when viewed in cross section taken perpendicular to the longitudinal axis, the elliptical shape having a major axis and a minor axis, each cutting edge being located at the outer surface adjacent the major axis of the elliptical shape.

15. The tissue sampling device of claim 14 further comprising a cannula having a proximal end, a distal end, and an inner surface extending between the proximal end of the cannula and the distal end of the cannula and defining a passage, the inner surface having an elliptical shape when viewed in cross section taken perpendicular to the longitudinal axis, the cannula receiving the shaft with the inner surface of the cannula closely fitting the outer surface of the shaft.

16. A tissue sampling device for removing tissue from a target area in a body comprising:
a shaft having a proximal end, a distal end, and a central longitudinal axis extending from the proximal end to the distal end, the shaft also having a length extending in a direction along the longitudinal axis, an outer surface of the shaft extending lengthwise of the shaft,
the outer surface including two first portions extending lengthwise of the shaft and two second portions extending lengthwise of the shaft, each first portion of the outer surface being associated with a different second portion and being spaced apart from its associated second portion by a predetermined distance, each first portion of the outer surface at least partially defining a cutting edge extending in a straight line lengthwise of the shaft,
the shaft further including two tissue-receiving surfaces extending lengthwise of the shaft, each first portion of the outer surface and its associated second portion being associated with a different tissue-receiving surface, each tissue-receiving surface defining a depression for receiving a sample of tissue removed from the target area by the cutting edge defined by its associated first portion of the outer surface when the shaft is rotated about its longitudinal axis in the target area, each tissue-receiving surface extending from adjacent its associated first portion of the outer surface toward its associated second portion of the outer surface for a majority of the predetermined distance between its associated first portion and its associated second portion and providing a continuous surface free of any opening,
each tissue-receiving surface and each cutting edge being movable radially relative to a portion of the shaft adjacent the proximal end of the shaft while maintaining the cutting edge in a straight line.

17. The tissue sampling device of claim 16 wherein the two tissue-receiving surfaces are (a) presented toward each other and (b) movable relative to each other.

18. The tissue sampling device of claim 17 wherein the two tissue-receiving surfaces are movable in translation relative to each other.

19. The tissue sampling device of claim 17 wherein the two tissue-receiving surfaces are movable pivotally relative to each other.

* * * * *